US012727809B2

(12) United States Patent
Lee et al.

(10) Patent No.: US 12,727,809 B2
(45) Date of Patent: Sep. 8, 2026

(54) WEARABLE DEVICE AND METHOD OF DETECTING ATRIAL FIBRILLATION

(71) Applicant: SAMSUNG ELECTRONICS CO., LTD., Suwon-si (KR)

(72) Inventors: Soyoung Lee, Suwon-si (KR); Jinseok Lee, Yongin-si (KR); Sang Kyu Kim, Suwon-si (KR); Yongbin Lee, Yongin-si (KR); Hong Soon Rhee, Suwon-si (KR)

(73) Assignees: SAMSUNG ELECTRONICS CO., LTD., Suwon-si (KR); UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 0 days.

(21) Appl. No.: 18/883,205

(22) Filed: Sep. 12, 2024

(65) Prior Publication Data

US 2025/0082250 A1 Mar. 13, 2025

(30) Foreign Application Priority Data

Sep. 13, 2023 (KR) ........................ 10-2023-0122080
Nov. 23, 2023 (KR) ........................ 10-2023-0164844

(51) Int. Cl.
*A61B 5/361* (2021.01)
*A61B 5/024* (2006.01)

(52) U.S. Cl.
CPC .......... *A61B 5/361* (2021.01); *A61B 5/02416* (2013.01)

(58) Field of Classification Search
CPC ... A61B 5/361; A61B 5/02416; A61B 5/7257; A61B 5/02438; A61B 5/681; A61B 5/721; A61B 5/0205; A61B 5/0002; A61B 5/11; A61B 5/1126; A61B 5/33; A61B 5/6802; A61B 2560/0462
See application file for complete search history.

(56) References Cited

U.S. PATENT DOCUMENTS

| | | | | |
|---|---|---|---|---|
| 7,104,959 | B2 * | 9/2006 | Yasushi .................. | A61B 5/352 600/509 |
| 9,986,923 | B2 * | 6/2018 | Mestha .................. | A61B 5/725 |
| 10,390,758 | B2 | 8/2019 | Wiggings et al. | |
| 10,398,381 | B1 | 9/2019 | Heneghan et al. | |

(Continued)

FOREIGN PATENT DOCUMENTS

| | | | |
|---|---|---|---|
| CN | 109953756 A | 7/2019 | |
| CN | 111589093 B | 1/2023 | |
| WO | WO-2018119316 A1 * | 6/2018 | ............ G06N 3/044 |

OTHER PUBLICATIONS

David Pollreisz et al., "Detection and Removal of Motion Artifacts in PPG Signals", Mobile Networks and Applications (2022) 27:728-738, Published online: Aug. 8, 2019, 11 Pages Total.

(Continued)

*Primary Examiner* — Oommen Jacob
(74) *Attorney, Agent, or Firm* — Sughrue Mion, PLLC

(57) ABSTRACT

A method of detecting atrial fibrillation includes receiving a photoplethysmogram (PPG) signal from a first sensor of a wearable device, detecting a heart rate from the PPG signal based on a window power spectrum analysis of the PPG signal, and detecting atrial fibrillation based on the heart rate.

17 Claims, 20 Drawing Sheets

(56) References Cited

U.S. PATENT DOCUMENTS

| | | | | |
|---|---|---|---|---|
| 10,987,054 | B2 | 4/2021 | Pandya et al. | |
| 11,291,401 | B2 | 4/2022 | Velo | |
| 2014/0330134 | A1* | 11/2014 | Chon | A61B 5/361<br>600/479 |
| 2016/0361021 | A1* | 12/2016 | Salehizadeh | A61B 5/02427 |
| 2017/0020399 | A1* | 1/2017 | Shemesh | A61B 5/0245 |
| 2017/0135593 | A1* | 5/2017 | Huang | A61B 5/02438 |
| 2017/0164847 | A1* | 6/2017 | Pande | A61B 5/721 |
| 2017/0296075 | A1* | 10/2017 | Loseu | A61B 5/02416 |
| 2019/0133468 | A1* | 5/2019 | Aliamiri | A61B 5/7221 |
| 2019/0328243 | A1* | 10/2019 | Nemati | A61B 5/7221 |
| 2023/0165508 | A1 | 6/2023 | Kentta et al. | |
| 2023/0225634 | A1 | 7/2023 | Wright et al. | |
| 2023/0346235 | A1* | 11/2023 | Chang | A61B 5/721 |
| 2025/0082250 | A1* | 3/2025 | Lee | A61B 5/02416 |

OTHER PUBLICATIONS

Tharoeun Thap et al., "High-Resolution Time-Frequency Spectrum-Based Lung Function Test from a Smartphone Microphone", Sensors 2016, 16 Pages Total.

Md-Billal Hossain et al., "Robust ECG Denoising Technique Using Variable Frequency Complex Demodulation", Nov. 21, 2020, 25 Pages Total.

Syed Khairul Bashar et al., "VERB: VFCDM-Based Electrocardiogram Reconstruction and Beat Detection Algorithm", vol. 7, 2019, 11 Pages Total.

* cited by examiner

WEARABLE DEVICE AND METHOD OF DETECTING ATRIAL FIBRILLATION

CROSS-REFERENCE TO RELATED APPLICATIONS

This application is based on and claims priority under 35 U.S.C. § 119 to Korean Patent Application No. 10-2023-0122080, filed on Sep. 13, 2023 and to Korean Patent Application No. 10-2023-0164844, filed on Nov. 23, 2023, in the Korean Intellectual Property Office, the disclosures of each of which being incorporated by reference herein in their entireties.

BACKGROUND

Methods, apparatuses and devices consistent with the present disclosure relate to a medical monitoring method and device and, more particularly, to a wearable device and method for detecting atrial fibrillation.

Atrial fibrillation (AF) is a heart disease that causes fast and irregular heartbeats that occur within the atria and may lead to serious health risks such as blood clots and stroke. Detection algorithms based on various biological signals such as electrocardiogram (ECG) or photoplethysmogram (PPG) signals have been developed to detect irregular heart rhythms such as AF or atrial flutter (AFL). ECG-based detection has high accuracy but requires multiple electrodes to be attached to a patient to measure an ECG signal, and multiple electrodes need to be in contact with the human skin, and thus continuous monitoring is difficult in wearable devices. PPG-based detection is advantageous for continuous monitoring but vulnerable to motion artifacts.

SUMMARY

It is an aspect to provide a wearable device and method for atrial fibrillation detection that improves the accuracy of atrial fibrillation diagnosis by continuously monitoring atrial fibrillation based on photoplethysmogram (PPG) and electrocardiogram (ECG) signals.

According to an aspect of one or more embodiments, there is provided a method of detecting atrial fibrillation, the method comprising receiving a photoplethysmogram (PPG) signal from a first sensor of a wearable device; detecting a heart rate from the PPG signal based on a window power spectrum analysis of the PPG signal; and detecting atrial fibrillation based on the heart rate.

According to another aspect of one or more embodiments, there is provided a method of detecting atrial fibrillation, the method comprising obtaining a photoplethysmogram (PPG) signal from a first sensor of a wearable device; obtaining a motion detection signal from a second sensor of the wearable device; determining whether there is motion exceeding a reference value, based on the motion detection signal; detecting a heart rate from the PPG signal based on a peak-peak interval (PPI) of the PPG signal when the motion does not exceed the reference value and based on power spectrum analysis in a frequency domain of the PPG signal when the motion exceeds the reference value; and detecting atrial fibrillation based on the heart rate.

According to yet another aspect of one or more embodiments, there is provided a wearable device comprising a first sensor configured to sense a pulse wave of a user and generate a photoplethysmogram (PPG) signal based on the pulse wave; a second sensor configured to sense motion of the user and generate a motion detection signal; a memory storing program code; and at least one processor configured to access the memory to execute the program code, wherein the program code causes at least one of the at least one processor to detect a heart rate based on a peak-peak interval (PPI) of the PPG signal when the second sensor senses no motion and based on power spectrum analysis of the PPG signal in a frequency domain when is the second sensor senses motion, and wherein the program code causes at least one of the at least one processor to detect atrial fibrillation based on the heart rate.

BRIEF DESCRIPTION OF THE DRAWINGS

Various embodiments will be more clearly understood from the following detailed description taken in conjunction with the accompanying drawings, in which.

DETAILED DESCRIPTION

Hereinafter, various embodiments will be described in detail with reference to the attached drawings.

Figure 1:
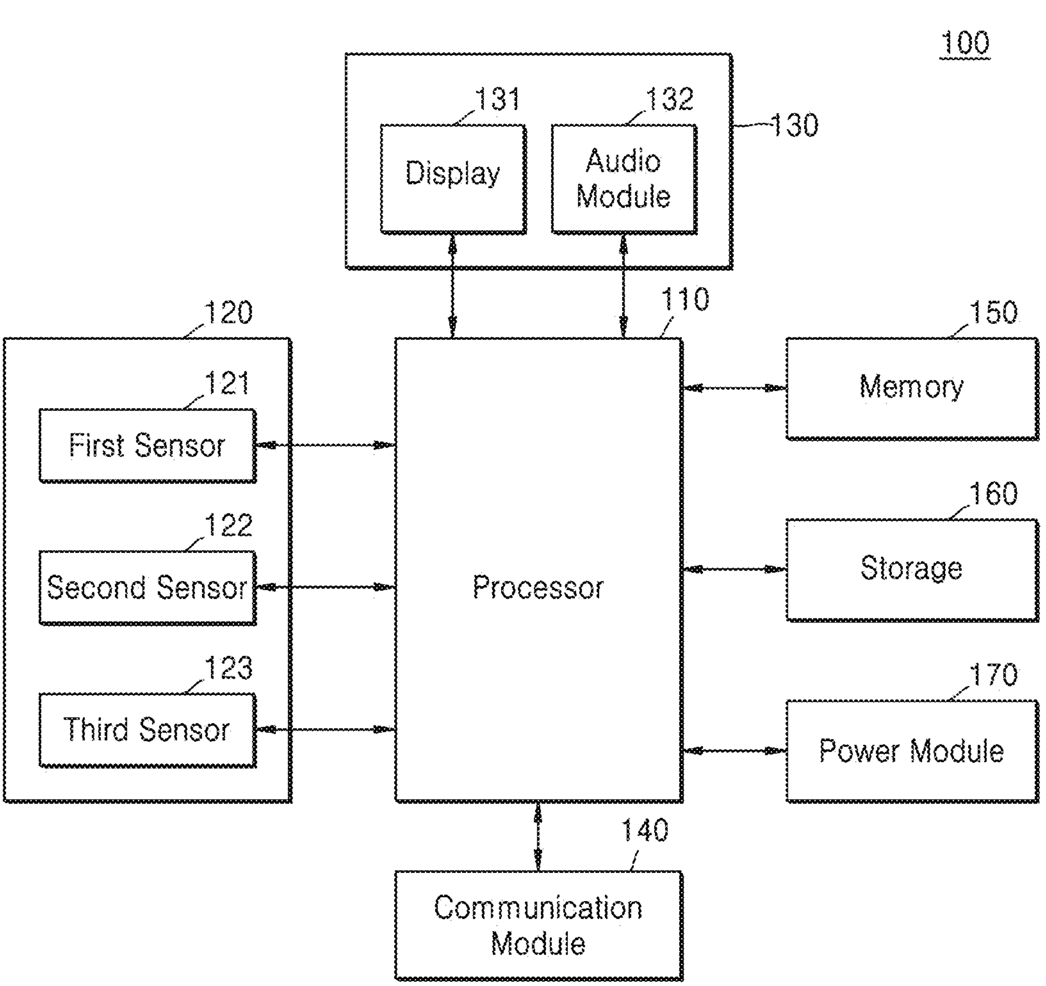
FIG. 1 is a block diagram showing an electronic device, according to an embodiment.

FIG. 1 shows an electronic device, according to an embodiment.

Referring to FIG. 1, an electronic device 100 may include a processor 110, a sensor module 120, an input/output device 130, a communication module 140, a memory 150, a storage 160, and a power module 170. The electronic device 100 is not limited thereto and may further include various components.

The electronic device 100 may be a user-wearable device for monitoring a biological signal of a user. The user may wear the electronic device 100 on a part of the body such as the arm, leg, or neck. The electronic device 100 may sense biological signals of the user by using a sensor provided in the sensor module 120 (e.g., a first sensor 121, a second sensor 122, and a third sensor 123) and monitor a health status of the user.

The sensor module 120 may include a plurality of sensors, for example, the first sensor 121, the second sensor 122, and the third sensor 123. The first sensor 121, the second sensor 122, and the third sensor 123 may sense different biological signals.

The first sensor 121 may be a photoplethysmogram (PPG) sensor. The PPG sensor may generate a PPG signal by measuring a pulse wave of the user. The PPG sensor may measure the pulse wave of the user based on a principle that an amount of absorbed light varies depending on a heartbeat when light is irradiated to the skin of the user.

Figure 2:
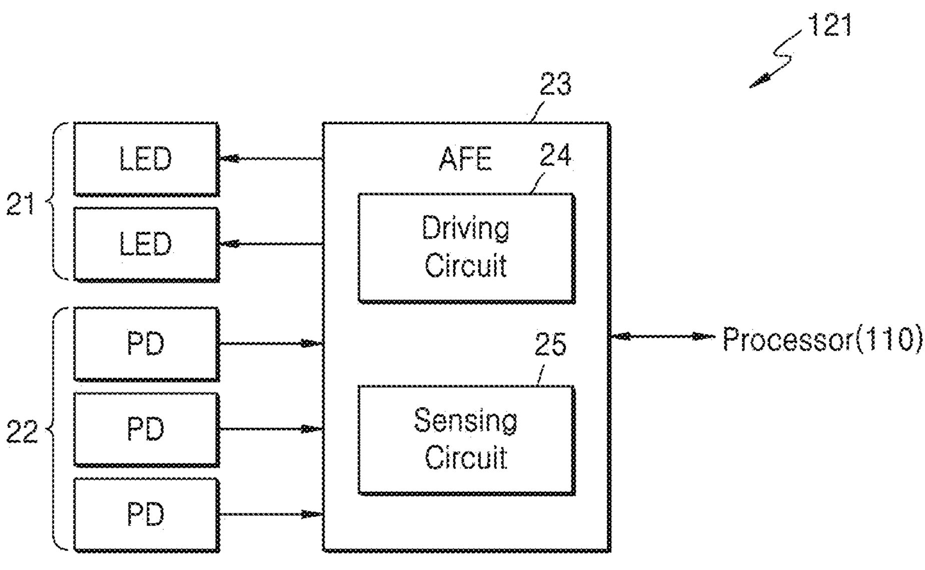
FIG. 2 is a block diagram showing a first sensor, according to an embodiment.

Referring to FIG. 2, the first sensor 121 may include a light emitting module 21, a light receiving module 22, and an analog-front end (AFE) 23. The light emitting module 21 may include one or more light emitting elements. For example, the light emitting module 21 may include a light emitting diode (LED). The light receiving module 22 may include one or more photodiodes (PD). For example, the light receiving module 22 may include an optical sensor including a photo detector. In FIG. 2, the light emitting module 21 is shown as including two LEDs, and the light receiving module 22 is shown as including three PDs, but embodiments are not limited thereto, and the number of light emitting elements and the number of PDs may each vary.

In response to a measurement request from the processor 110, the AFE 23 may drive the light emitting module 21 and transmit a sensing signal received from the light receiving module 22 to the processor 110. The AFE 23 may include a driving circuit 24 and a sensing circuit 25.

The driving circuit 24 may provide a driving signal to the light emitting element. For example, the driving circuit 24 may provide a driving current to LEDs. The driving circuit 24 may include a metal oxide silicon field effect transistor (MOSFET) and a digital-to-analog converter configured to control current.

The sensing circuit 25 may convert the reflected light measured by the PD into a PPG signal. The sensing circuit 25 may include an amplifier, a filter, and an analog-to-digital converter. For example, the amplifier may be implemented as a transimpedance amplifier.

The sensing circuit 25 may convert the measured reflected light into a voltage signal by using the amplifier and filter the converted voltage signal by using a low-pass filter. For example, the low-pass filter may block a frequency component greater than 5 Hz (Hertz). The analog-to-digital converter may convert the filtered signal into a digital signal, such as a PPG signal.

The first sensor 121 may continuously measure the pulse wave of the user (for example, continuously as long as there is no interruption by the user) and generate the PPG signal. The light emitting module 21 and the light receiving module 22 of the first sensor 121 may be in contact with the skin of the user, and thus the first sensor 121 may measure the pulse wave of the user. For example, the first sensor 121 may continuously measure pulse waves without awareness of the user.

The first sensor 121 may transfer the PPG signal to the processor 110. For example, transmission of the PPG signal to the processor 110 may be performed based on a Serial Peripheral Interface (SPI)-based interface. However, embodiments are not limited thereto, and an inter-integrated circuit (I2C), an improved inter integrated circuit (I3C), a mobile industry processor interface (MIPI), a universal asynchronous receiver/transmitter (UART), an embedded display port (eDP), low-voltage differential signaling (LVDS), a universal serial interface (USI), an ultra path interface (UPI), and/or enhanced reduced voltage differential signal transmission (eRVDS) may be used between the first sensor 121 and the processor 110.

Continuing to refer to FIG. 1, the second sensor 122 may be an electrocardiogram (ECG) sensor. The ECG sensor may generate an ECG signal by measuring an ECG of the user. The ECG sensor may include a plurality of electrodes (or a plurality of pads) (e.g., 35*a* in FIGS. 3A and 35*b* in FIG. 3B) and an AFE.

An electrical signal may be applied to the skin of the user through at least one electrode of the plurality of electrodes, and an ECG signal representing electrical activity in the heart may be output through at least one other electrode of the plurality of electrodes.

At least one electrode of the plurality of electrodes may be disposed in contact with the skin of the user, and at least one other electrode of the plurality of electrodes may be in contact with the skin of the user when the user intentionally touches the electrode with a part of the body (for example, a finger). Accordingly, the second sensor 122 may measure the ECG in response to a request of the user (e.g., touch) or may measure the ECG in response to a request from the processor 110. The AFE may generate an ECG signal by amplifying and analog-to-digital converting the measured electrical signal.

The second sensor 122 may transfer the ECG signal to the processor 110. For example, transmission of the ECG signal to the processor 110 may be performed based on an SPI-based interface. However, embodiments are not limited thereto, and one of the various high-speed serial interface (HSSI) methods described above may be applied between the second sensor 122 and the processor 110.

The third sensor 123 may be a motion detection sensor. For example, the third sensor 123 may be implemented as an inertial measurement unit (IMU). The IMU may include an acceleration sensor and a gyroscope. The IMU may further include a geomagnetic sensor. The third sensor 123 may generate an IMU signal such as a 3-axis accelerometer signal by measuring a user motion (hereinafter referred to as motion), for example, a posture change, a speed of change of position movement, or an amount of displacement. The IMU signal may be referred to as a motion detection signal. The third sensor 123 may continuously measure the user motion and generate the IMU signal.

The third sensor 123 may transfer the IMU signal to the processor 110. For example, transmission of the IMU signal to the processor 110 may be performed based on an SPI-based interface. However, embodiments are not limited thereto, and one of the various HSSI methods described above may be applied between the third sensor 123 and the processor 110.

In an embodiment, the sensor module 120 may further include another biometric sensor. For example, the sensor module 120 may further include a sensor configured to measure bio-impedance of the user and a sensor configured to sense a state or change of sweat, blood, urine, and/or the iris. For example, the sensor module 120 may further include a galvanic skin response (GSR) sensor, an electrodermal activity (EDA) sensor, a ballistocardiogram (BCG)

sensor, a sweat sensor for sensing hydration or dehydration, an iris sensor, and/or a body temperature sensor.

The processor 110 may control the overall operation of the electronic device 100 and control components such as the sensor module 120, the input/output device 130, the communication module 140, the memory 150, the storage 160, and the power module 170. In an embodiment, the processor 110 may include a micro control unit (MCU). However, embodiments are not limited thereto, and the processor 110 may include processing circuitry such as a central processing unit (CPU) or a micro processing unit (MPU). In some embodiments, the processor 110 may include at least one processor and at least one of the at least one processor may perform an operation of the operations described below with respect to FIGS. 5-6, 10, 12, and 14-16. In some embodiments, the processor 110 may include a plurality of processors 110. In some embodiments, the plurality of processors 110 may execute respective operations described below with respect to FIGS. 5-6, 10, 12, and 14-16. In some embodiments, each one of the plurality of processors may execute a portion of the operations described below with respect to FIGS. 5-6, 10, 12, and 14-16. In some embodiments, the processor 110 may include a plurality of cores, where each core is configured to execute one or more operations described below with respect to FIGS. 5-6, 10, 12, and 14-16.

The processor 110 may process biological signals received from the sensor module 120, such as PPG signals, ECG signals, and IMU signals, and monitor a health status of the user based on the signals.

In an embodiment, the processor 110 may detect atrial fibrillation based on the PPG signal. The processor 110 may monitor whether atrial fibrillation occurs in real time based on the PPG signal continuously received from the first sensor 121. The processor 110 may detect a heart rate based on the PPG signal and detect atrial fibrillation based on the detected heart rate. For example, the processor 110 may perform stochastic analysis on a plurality of heart rates detected continuously and determine whether atrial fibrillation occurs based on the analysis result. For example, Shanon entropy, sample entropy, and/or root mean square of the successive difference (RMSSD) may be used as the stochastic analysis.

When atrial fibrillation is detected, that is, when it is determined that atrial fibrillation occurs, the processor 110 may generate an event indicating that atrial fibrillation occurs and output an ECG measurement request signal (or alarm) to a user. The processor 110 may control the second sensor 122 to measure the ECG.

The processor 110 may transmit the ECG signal received from the second sensor 122 to an external device through the communication module 140. In an embodiment, the processor 110 may signal-process the ECG signal (sampling, compression, and the like) to generate ECG data and transmit the ECG data to an external device. For example, the ECG signal (or ECG data) may be transmitted to a smartphone and transmitted to a medical staff server through the smartphone. Medical staff may diagnose whether atrial fibrillation occurs based on the ECG signal.

In an embodiment, the processor 110 may detect a heart rate from the PPG signal based on a window power spectrum analysis of the PPG signal and detect atrial fibrillation based on the detected heart rate. In an embodiment, when determining that motion occurs, the processor 110 may cancel motion artifacts from a motion PPG signal based on the IMU signal. Such analysis of the PPG signal and cancellation of motion artifacts may be performed in the frequency domain. This analysis and operation will be described in detail later.

In an embodiment, the processor 110 may determine whether motion occurs based on the IMU signal. For example, when determining that there is no motion (e.g., the magnitude of motion based on the IMU signal is less than or equal to a reference value), the processor 110 may detect a heart rate based on the peak-peak interval (PPI) characteristics of the PPG signal, and when determining that there is motion (e.g., when the magnitude of motion based on the IMU signal exceeds the reference value), the processor 110 may detect the heart rate from the PPG signal based on the window power spectrum analysis of the PPG signal, as described above.

In an embodiment, the processor 110 may select highly reliable heart rates from among the detected heart rates by using a finite state machine (FSM). In other words, the processor 110 may discard unreliable heart rates. The processor 110 may detect atrial fibrillation based on highly reliable heart rates.

The input/output device 130 may include various devices configured to receive user input and may include various devices configured to provide information, notifications, and the like to a user. The input/output device 130 may include a display 131 and an audio module 132. The input/output device 130 may further include devices such as a vibration module or an input key.

The display 131 may display a variety of information under control by the processor 110. For example, the display 131 may display biometric information of the user, such as a heart rate or oxygen saturation. The display 131 may display atrial fibrillation detection information (whether atrial fibrillation occurs), arrhythmia information (presence of arrhythmia and/or type of arrhythmia), or suspected disease information. The display 131 may display information requesting a user action, for example, information requesting that a finger touch an ECG measurement electrode for ECG measurement, or recommendation information on a hospital visit. For example, when atrial fibrillation is detected based on the PPG signal, the display 131 may display event information indicating that atrial fibrillation occurs and display information requesting the user to measure ECG and touch the ECG measurement electrode with the finger to measure ECG.

The display 131 may include at least one of various displays such as a liquid crystal display (LCD), a thin film transistor LCD (TFT-LCD), an organic light emitting diode (OLED) display, a light emitting diode (LED) display, an active matrix organic LED (AMOLED) display, a micro LED display, a mini LED display, a flexible display, and a 3-dimensional display. In an embodiment, the display 131 may be implemented in the form of a touch screen. In an embodiment, the display 131 may be implemented as a fixed display or a flexible display.

The audio module 132 may output sound, and for example, the audio module 132 may include at least one of an audio codec, a microphone (MIC), a receiver, an earphones output, or a speaker. The audio module 132 may output, as an audio signal, information related to a physical condition of a user, information related to abnormal signs of a health condition of the user, or additional information, based on the acquired biometric information and/or suspected disease information. For example, when atrial fibrillation is detected, the audio module 132 may output an alarm indicating that atrial fibrillation occurs.

The communication module 140 may communicate with an external device. In an embodiment, the communication module 140 may include a Bluetooth module. However, embodiments are not limited thereto, and for example, in some embodiments, the communication module 140 may include a communication interface accessible to wireless local area network (WLAN) such as wireless fidelity (Wi-fi), a wireless personal area network (WPAN), a wireless universal serial bus (wireless USB), Zigbee, near field communication (NFC), and radio-frequency identification (RFID), or a mobile communication network such as 3rd generation (3G), 4th generation (4G), or long term evolution (LTE). In an embodiment, the communication module 140 may further include a communication interface accessible to a wired local area network.

The communication module 140 may transmit information related to the physical condition of the user, information related to abnormal signs of the health condition of the user, and/or additional information to an external electronic device (e.g., a smartphone of the user). The communication module 140 may transmit measured biological signals, such as ECG data, to an external electronic device. An external electronic device may transmit the biological signal to a medical server. In an embodiment, the communication module 140 may access a network (e.g., an access point or a mobile communication network) and transmit ECG data directly to a medical server.

The memory 150 may be implemented as volatile memory such as dynamic random access memory (DRAM) and static RAM (SRAM), or a non-volatile resistive memory such as phase change RAM (PRAM) and resistive RAM (ReRAM). In an embodiment, the memory 150 may be integrated into the processor 110. In an embodiment, the memory 150 may include a plurality of memories 150. The plurality of memories 150 may be volatile memory or non-volatile memory, or different combinations thereof.

An operating program, program code, or application program executed by the processor 110 may be loaded into the memory 150 and executed. For example, a program including program code that, when executed, implement the functions of the processor 110 described above may be loaded into the memory 150 and executed by the processor 110.

The memory 150 may store data to be processed by the processor 110 or data generated by the processor 110. For example, the memory 150 may temporarily store biometric signal measurement records (e.g., the number of measurements or measurement time), biometric information of the user, and suspected disease information.

The storage 160 may be implemented as a non-volatile memory device such as a NAND flash or a resistive memory, and for example, the storage 160 may be provided as a memory card (an MMC card, eMMC card, SD, or micro SD card) or the like. The storage 160 may store data generated by the processor 110. The storage 160 may store biometric signal measurement records (e.g., the number of measurements or measurement time), biometric information of the user, and suspected disease information. In an embodiment, the storage 160 may store a measured biological signal, for example, an ECG signal.

A power module 170 may include a battery, a charging circuit, and a power management unit (PMU). In an embodiment, the PMU may be integrated into the processor 110. The power module 170 may generate and provide power used by the electronic device 100 based on power provided from a battery or an external power source. The power module 170 may charge the battery based on the external power source. The PMU may manage power of components. For example, the PMU may provide power to a component and determine the level (e.g., voltage level) of power provided to the component or an operating frequency based on an operating state of the electronic device 100 or an operating state of each component. The PMU may block power.

Figure 3A:
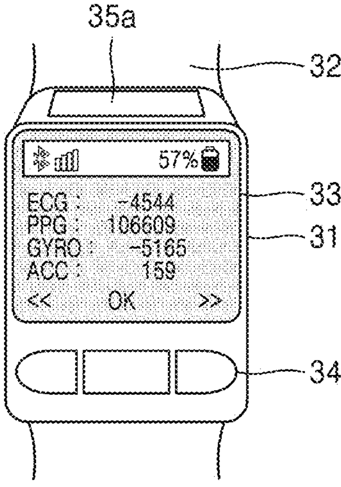
FIGS. 3A and 3B show an example in which an electronic device is implemented as a wearable device, according to some embodiments.
Figure 3B:
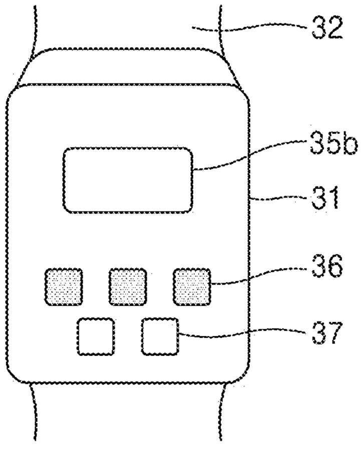

FIGS. 3A and 3B show an example in which an electronic device is implemented as a wearable device, according to an embodiment. FIG. 3A shows a first surface (e.g., front surface) of the electronic device 100, and FIG. 3B shows a second surface (e.g., rear surface) of the electronic device 100.

Referring to FIGS. 3A and 3B, the electronic device 100 may be, for example, a watch-type wearable device wearable on the wrist of a user or a wearable device wearable on other parts of the human body (e.g., the head, forearm, thigh, or other parts of the human body for measuring an ECG).

The electronic device 100 may include a display 33, an input button 34, a plurality of electrodes (e.g., a first electrode 35*a* and a second electrode 35*b*, etc.), at least one light emitting element 36, and at least one light receiving element 37 that may be located in a housing 31 forming the outer appearance of the electronic device 100. A strap 32 that assists the electronic device 100 in being worn on the body of the user may be connected to the housing 31. Some components described with reference to FIG. 1, for example, the processor 110, the communication module 140, the third sensor 123, the audio module 132, the memory 150, the storage 160, and the power module 170, may be provided inside the housing 31.

The first electrode 35*a* and the second electrode 35*b* may be electrodes for ECG measurement. The first electrode 35*a* may be disposed on the first surface, and the second electrode 35*b* may be disposed on the second surface. The at least one light emitting element 36 and the at least one light receiving element 37 may be disposed on the second surface. The at least one light emitting element 36 and the at least one light receiving element 37 may be elements configured to measure pulse waves of the user and may be included in the first sensor 121 (in FIG. 1).

When the electronic device 100 is worn on the body part of the user, the second surface may be in contact with the skin of the user. Thus, the at least one light emitting element 36 and the at least one light receiving element 37 may always be in contact with the skin of the user. Accordingly, the first sensor 121 may continuously measure pulse waves.

The second electrode 35*b* is always in contact with the skin of the user when the electronic device 100 is worn. The first electrode 35*a* is not in contact with the skin of the user when the electronic device 100 is worn, unless there is an intentional action by the user. Therefore, when the user touches the first electrode 35*a* with a part of the body (e.g., a finger), the second sensor 122 may measure the ECG based on electrical signals through the first electrode 35*a* and the second electrode 35*b*.

Figure 4A:
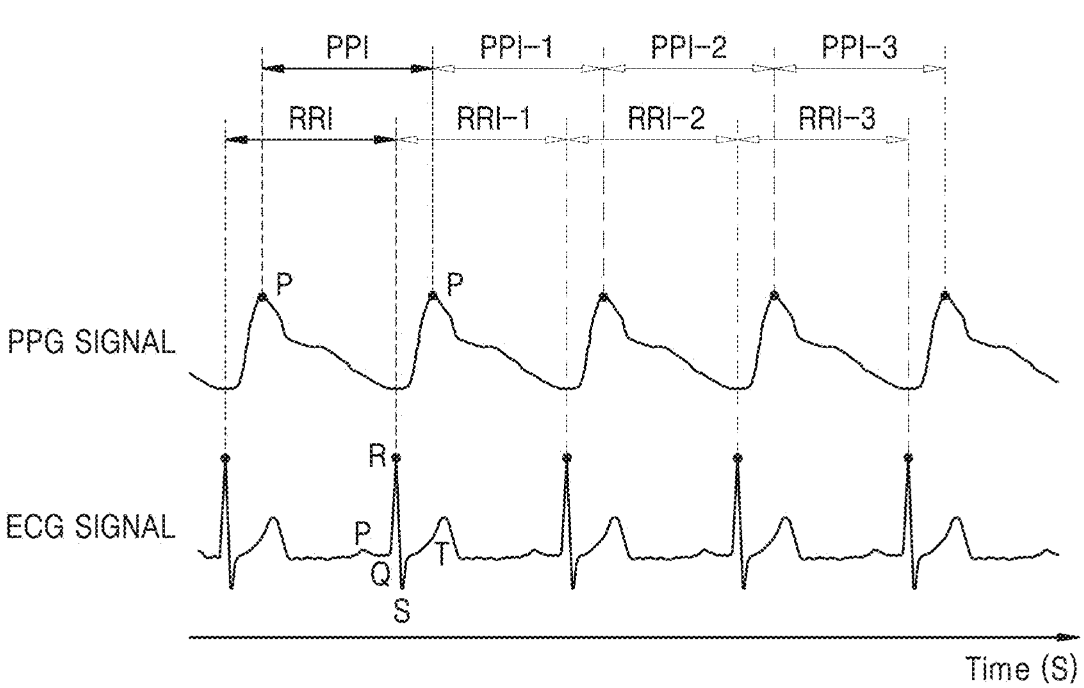
FIGS. 4A and 4B are signal waveform diagrams showing examples of a photoplethysmogram (PPG) signal and an electrocardiogram (ECG) signal.
Figure 4B:
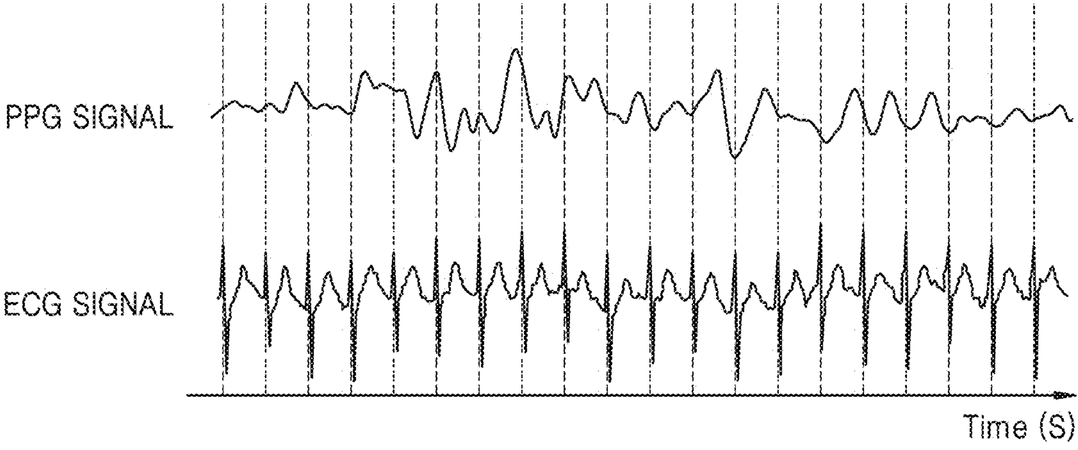

FIGS. 4A and 4B are signal waveform diagrams showing a PPG signal and an ECG signal. FIG. 4A shows a PPG signal and an ECG signal when there is no motion, and FIG. 4B shows a PPG signal and an ECG signal when there is motion. The horizontal axis represents time, and the vertical axis represents a size of a signal in voltage.

Referring to FIG. 4A, the ECG signal may include P-wave (P), Q peak (Q), R peak (R), S peak(S), and T-wave (T), which are repeatedly generated. The ECG signal includes prominent characteristics known as the QRS complex, which represents a primary pumping contraction of the heart. The R peak (R) in the ECG signal is used by a heart rate algorithm to measure the time at which the R peak (R)

occurs between pulsating pulses. A duration between R peaks is referred to as an RR interval (RRI).

A PPG signal is used to represent the periodicity of a signal waveform and includes quasi-periodic pulses with peaks (P) and valleys for estimation of a heart rate. The duration between the peaks (P) of two adjacent pulses is referred to as a PP interval (PPI) and may be used as an indicator of a heart rate.

Referring to FIG. 4B, when there is motion, the PPG signal may be distorted by motion artifacts. Accordingly, it is difficult to detect peaks (P) in the PPG signal. On the other hand, the ECG signal has less distortion due to motion artifacts than the PPG signal, and the R peak (R) may be detected in a certain form.

Figure 5:
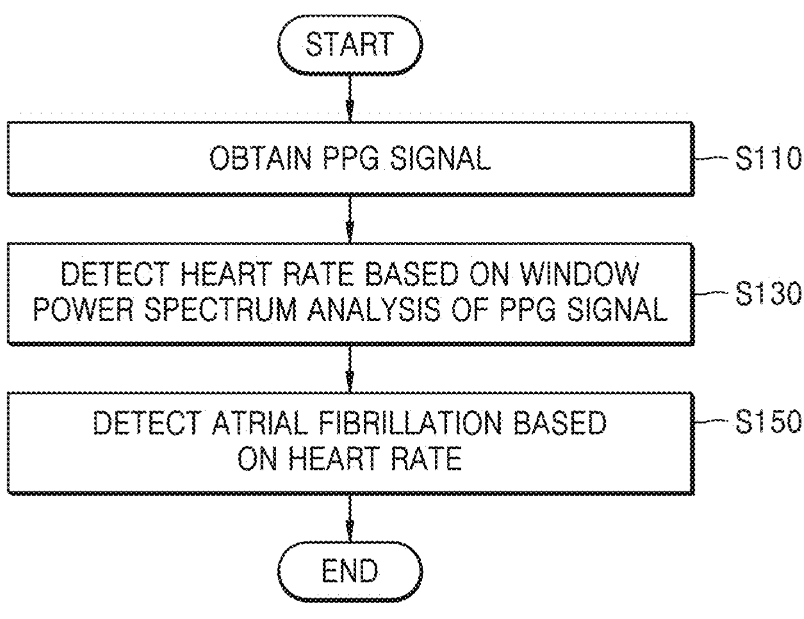
FIG. 5 is a flowchart showing a method of detecting atrial fibrillation, according to an embodiment.
Figure 6:
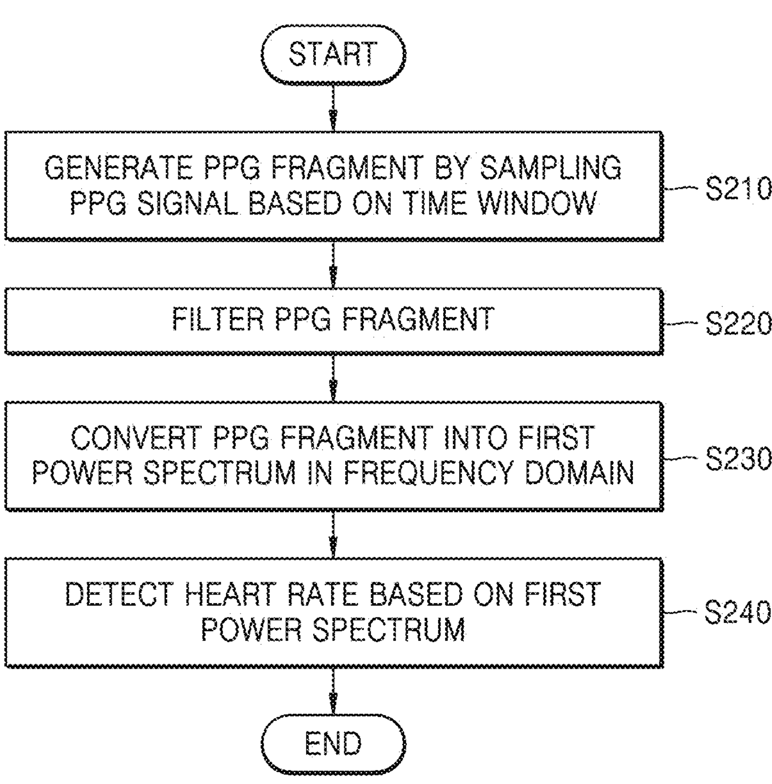
FIG. 6 is a flowchart showing window power spectrum analysis, according to an embodiment.

FIG. 5 is a flowchart illustrating a method of detecting atrial fibrillation, according to an embodiment, and FIG. 6 is a flowchart illustrating window power spectrum analysis in operation S130 of the method of FIG. 5 in more detail, according to an embodiment. The method of FIG. 5 may include operations S110, S130, and S150, and the flowchart illustrated in FIG. 6 may include operations S210 to S240. The operations S110, S130, S150, and S210 to S240 of the embodiment of FIGS. 5-6 may be performed by the electronic device 100 of FIGS. 1 and 3 and is described with reference to FIG. 1.

The electronic device 100 may obtain a PPG signal (S110). For example, the processor 110 may control the first sensor 121 to measure the pulse wave of the user to generate a PPG signal, and the PPG signal may be provided to the processor 110. The PPG signal may be obtained continuously.

The electronic device 100 may detect a heart rate based on window power spectrum analysis of the PPG signal (S130). Referring to FIG. 6, the processor 110 may generate a PPG fragment (e.g., PPG window data) by sampling the PPG signal based on a time window (S210). The time window may be set to a certain time. The processor 110 may filter the PPG fragment (S220). For example, the processor 110 may filter the PPG fragment by using a band pass filter. As a non-limiting example, the band pass filter may pass components in a frequency band of about 0.5 Hz to about 4 Hz. Accordingly, high frequency components, such as noise components, may be blocked in the PPG fragment. In an embodiment, operations S210 and S220 may be performed in the AFE 23 of the first sensor 121 (see FIG. 2). For example, a sensing circuit 25 of the AFE 23 may generate the PPG fragment by sampling the PPG signal based on the time window (S210) and block high-frequency components of the PPG fragment by using the band pass filter. The filtered PPG fragment may be transmitted to the processor 110.

The processor 110 may convert the PPG fragment, for example, a filtered PPG fragment, into a power spectrum in the frequency domain, for example, a first power spectrum (S230). In an embodiment, the processor 110 may convert the PPG fragment in the time domain into the first power spectrum in the frequency domain by using Fast Fourier Transform (FFT).

The processor 110 may detect a heart rate based on the first power spectrum (S240). For example, the processor 110 may detect a peak value in the first power spectrum and calculate the heart rate based on a frequency corresponding to the peak value. For example, when the first power spectrum has a peak value at 1.2 Hz, 72 beats per minute (BPM) may be calculated as the heart rate by multiplying 1.2 Hz by 60.

Continuing to refer to FIG. 5, the electronic device 100 may detect atrial fibrillation based on the detected heart rate (S150). In some embodiments, in operation S130, a plurality of heart rates corresponding to a plurality of PPG fragments may be detected, and the electronic device 100 may detect atrial fibrillation based on the plurality of heart rates. In an embodiment, the processor 110 may determine whether atrial fibrillation occurs through stochastic analysis.

Figure 7:
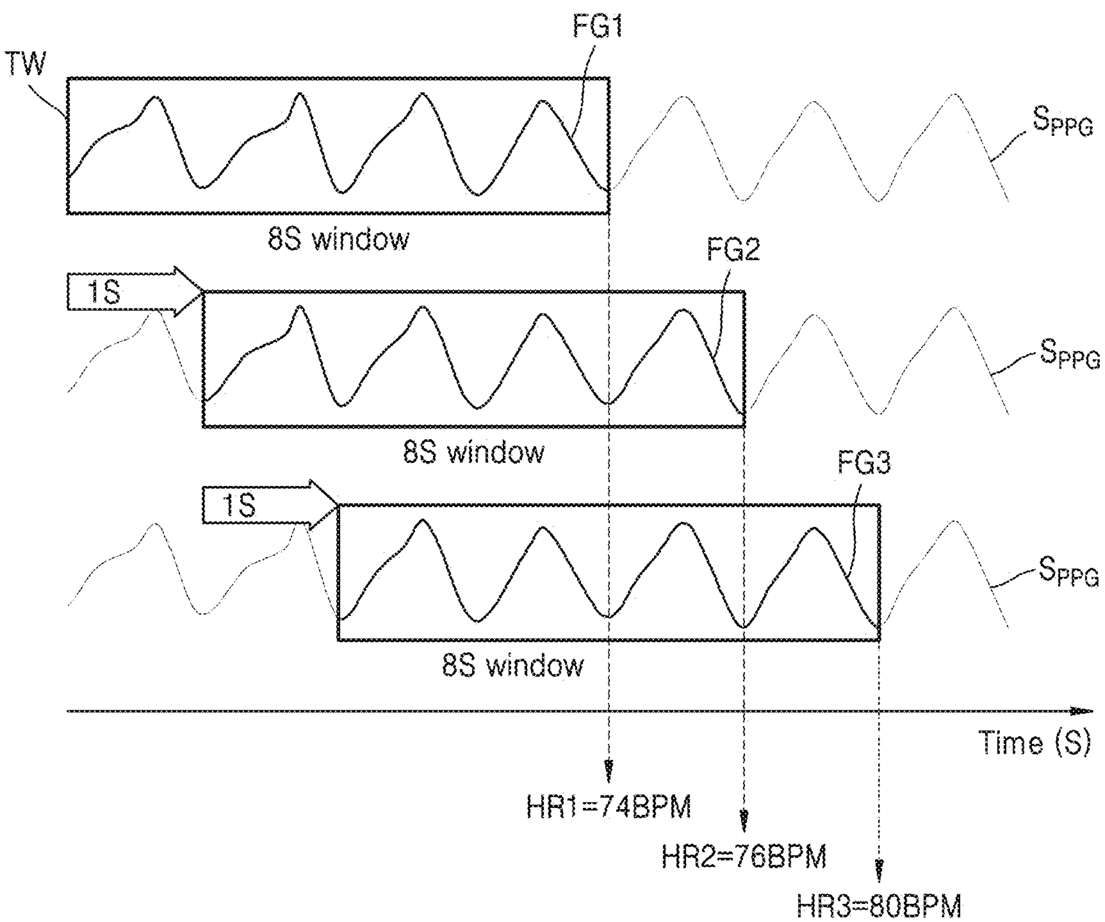
FIGS. 7 and 8 illustrate a method of detecting a plurality of heart rates through window power spectrum analysis, according to an embodiment.
Figure 8:
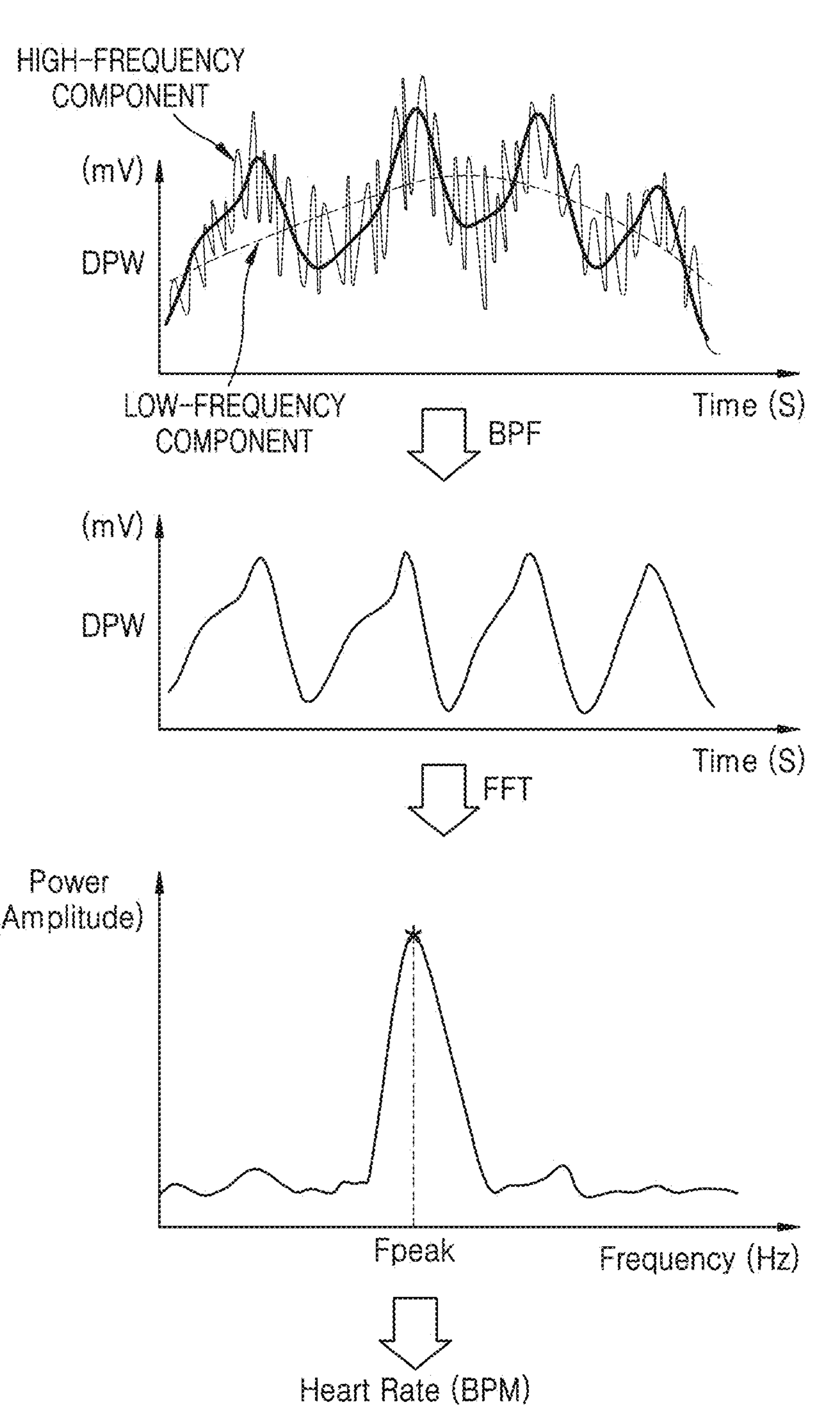

FIGS. 7 and 8 illustrate a method of detecting a plurality of heart rates through window power spectrum analysis, according to an embodiment. In an embodiment, the method of FIGS. 7 and 8 may be performed by the processor 110 (in FIG. 1).

Referring to FIG. 7, the processor 110 (in FIG. 1) may generate a PPG fragment by sampling the PPG signal SPPG based on a time window TW set to a certain time. The PPG fragment may include a sampled PPG signal. The time window TW may slide along the PPG signal SPPG at certain time intervals to generate a plurality of PPG fragments, for example, a first PPG fragment FG1, a second PPG fragment FG2, and a third PPG fragment FG3. The PPG signal SPPG may also be described as sliding in the time window TW. For example, the time window TW may be set to 8 seconds, and the time window TW may slide along the PPG signal SPPG and may sample the PPG signal SPPG at 1-second intervals. As illustrated in FIG. 7, the first PPG fragment FG1 may include, for example, four peaks (peaks one to four) of the PPG signal SPPG, the second PPG fragment FG2 may include, for example, four peaks (peaks two to five) of the PPG signal SPPG, and so on.

The processor 110 may calculate multiple heart rates through power spectrum analysis for each of a plurality of PPG fragments, for example, the first PPG fragment FG1, the second PPG fragment FG2, and the third PPG fragment FG3. Through power spectrum analysis, an average heart rate of a time window, rather than an instantaneous heart rate, may be calculated. For example, a first heart rate HR1 corresponding to the first PPG fragment FG1 may be calculated as 74 BPM, a second heart rate HR2 corresponding to the second PPG fragment FG2 may be calculated as 76 BPM, and a third heart rate HR3 corresponding to the third PPG fragment FG3 may be calculated as 80 BPM.

Referring to FIG. 8, signals of various frequency components including high-frequency components and low-frequency components of the PPG fragment FG may be provided. High-frequency components and low-frequency components may be cancelled from the PPG fragment through band-pass filtering (BPF). In other words, noise in high-frequency components and low-frequency components may be cancelled.

The filtered PPG fragment FG may be converted into a power spectrum in the frequency domain through FFT. The PPG signal is similar to a sine wave, and thus when the PPG fragment FG is converted into a power spectrum, the frequency with the greatest power (e.g., the peak of the power spectrum), that is, a peak frequency Fpeak, may be a frequency representing a heart rate. The peak frequency Fpeak multiplied by 60 may be calculated as the heart rate.

Figure 9:
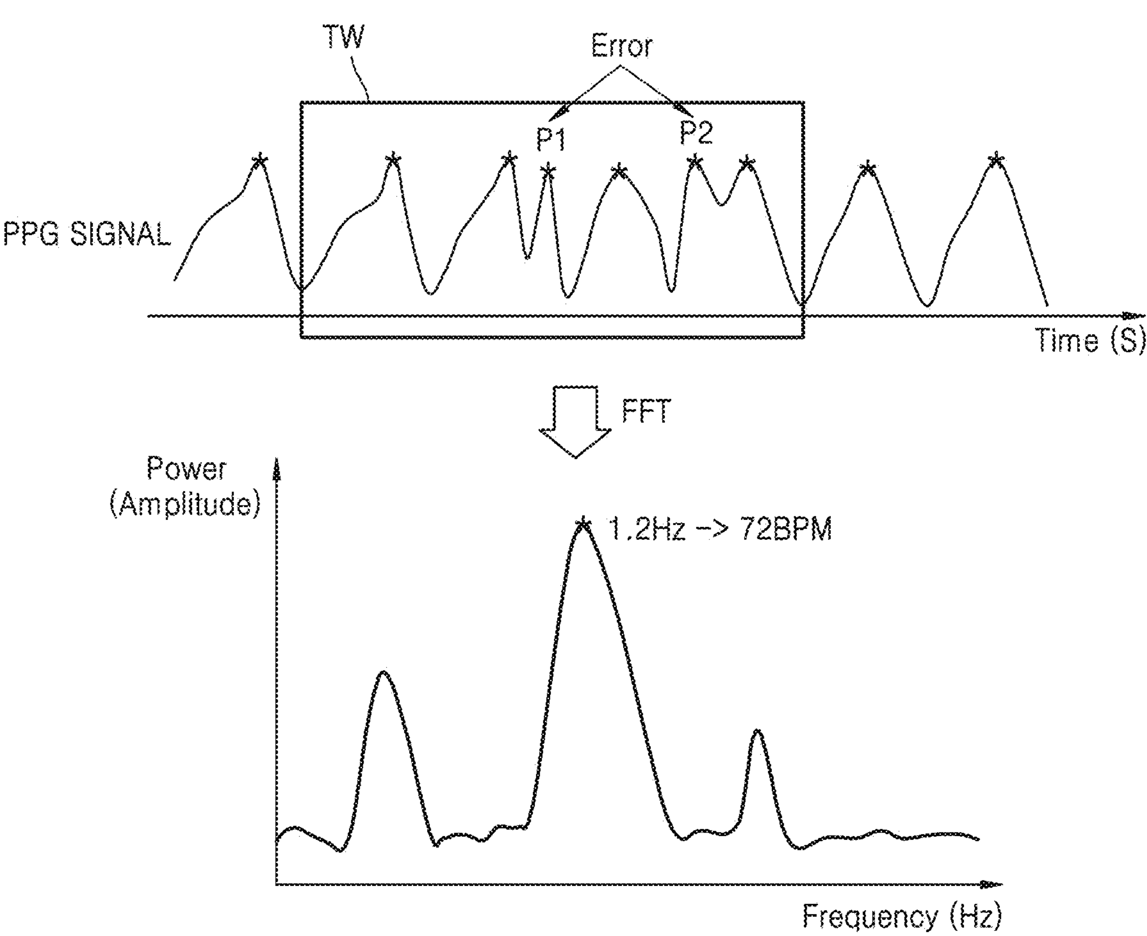
FIG. 9 shows a PPG signal in a time domain and a window power spectrum in a frequency domain when there is user motion.

FIG. 9 shows a PPG signal in the time domain and a power spectrum in the frequency domain when there is motion by a user.

When the user moves (and thus the electronic device 100 that the user is wearing moves), the PPG signal may be distorted by motion artifacts, and it may be difficult to detect peaks. For example, as shown, errors may occur in some peaks P1 and P2. In other words, the peaks P1 and P2 may be formed at the wrong time or a motion artifact may be inaccurately determined as a peak. Accordingly, it may be difficult to detect a heart rate based on the PPG signal, and the reliability of the detected heart rate may be reduced.

However, according to an embodiment, based on window power spectrum analysis, when PPG fragment FG is converted into a power spectrum in the frequency domain with a PPG window, the power spectrum may have large power at several frequencies due to motion artifacts. However, the peak frequency with the greatest power may be easily detected, and the peak frequency may be converted into a heart rate. Accordingly, a method of detecting a heart rate through window power spectrum analysis in the frequency domain may detect the heart rate easier than a method of detecting the heart rate based on the PPI characteristics of a PPG signal in the time domain and may have improved heart rate reliability.

Figure 10:
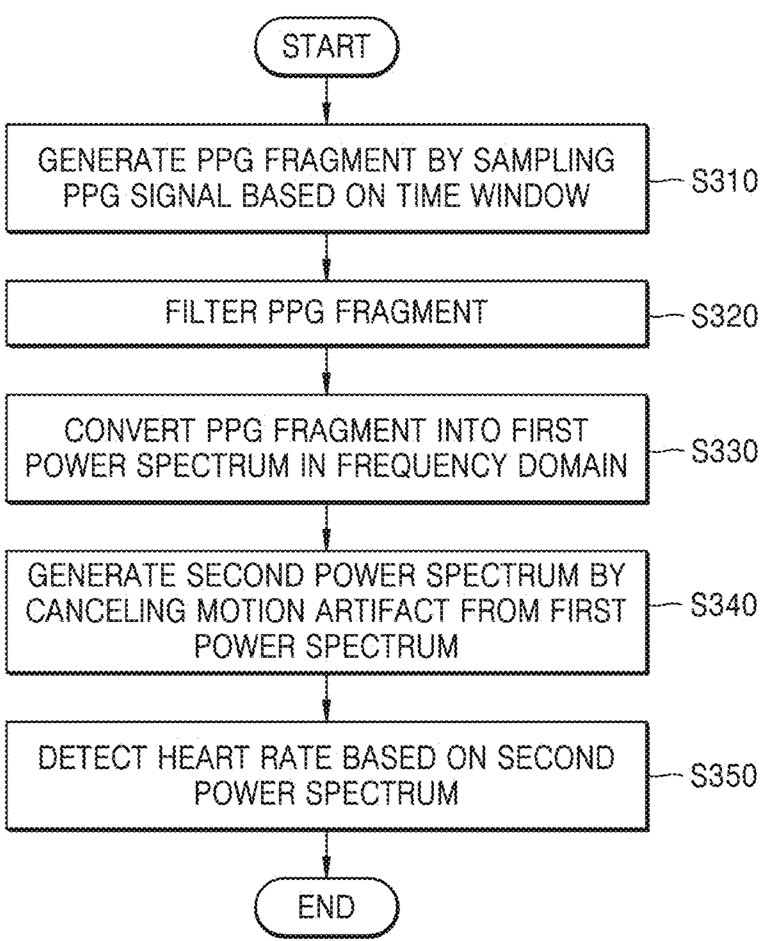
FIG. 10 is a flowchart showing window power spectrum analysis, according to an embodiment.

FIG. 10 is a flowchart showing window power spectrum analysis, according to an embodiment. The flowchart may include operations S310 to S350. The operations S310 to S350 of the embodiment of FIG. 10 may be performed by the electronic device 100 of FIGS. 1 and 3 and is described with reference to FIG. 1.

Referring to FIG. 10, the processor 110 may generate a PPG fragment by sampling a PPG signal based on a time window (S310). The time window may be set to a certain time. The processor 110 may filter the PPG fragment (S320). The processor 110 may convert the PPG fragment into a power spectrum in the frequency domain, for example, a first power spectrum (S330). In an embodiment, operations S310, S320, and S330 are respectively the same as operations S210, S220, and S230 of FIG. 6, and repeated descriptions thereof are omitted for conciseness. In an embodiment, in S310 or S320, the processor 110 may filter the PPG signal or the PPG fragment by using a finite impulse response (FIR) filter, a Wiener filter, and/or a Gaussian filter and cancel noise and/or motion artifacts. In an embodiment, operation S320 may be performed after operation S330. For example, the processor 110 may convert the PPG fragment into a first power spectrum and then perform filtering thereon in the frequency domain.

The processor 110 may generate a second power spectrum by canceling motion artifacts from the first power spectrum (S340). In an embodiment, the processor 110 may convert an IMU signal received from the third sensor 123 into a third power spectrum in the frequency domain and cancel the third power spectrum from the first power spectrum. Accordingly, the second power spectrum from which motion artifacts are cancelled may be generated.

The processor 110 may detect a heart rate based on the second power spectrum (S350). The processor 110 may calculate the heart rate based on the peak frequency with maximum power.

Figure 11:
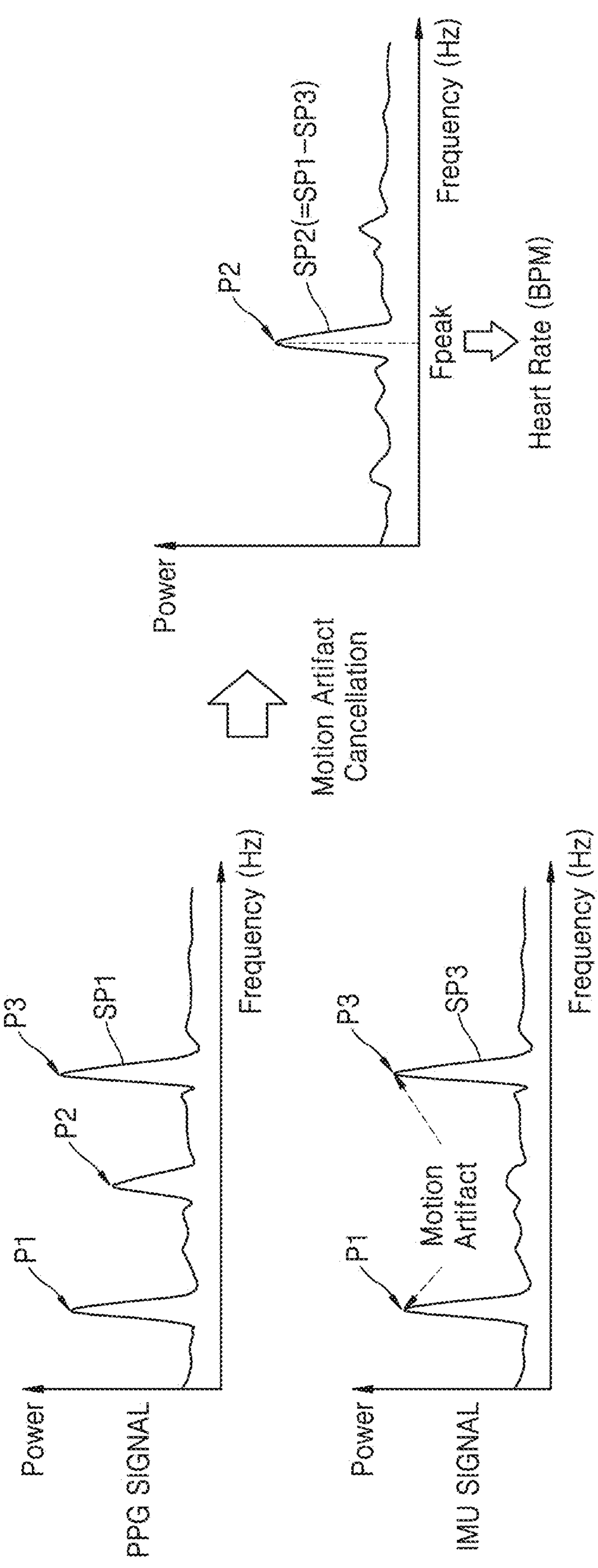
FIG. 11 shows cancellation of a motion artifact, according to an embodiment.

FIG. 11 shows cancellation of a motion artifact, according to an embodiment.

The motion artifact may have a frequency component that overlaps the PPG signal, and it is difficult to cancel the frequency component that overlaps the PPG signal by filtering, for example, filtering using a band pass filter in operation S220 or S320. Accordingly, when the PPG signal is distorted by motion artifacts, a power spectrum of the PPG signal (power spectrum of the PPG fragment), for example, a first power spectrum SP1 may include a plurality of peaks, for example, a first peak P1, a second peak P2, and a third peak P3. At least two of the first peak P1, the second peak P2, and the third peak P3 may be peaks caused by motion artifacts.

To determine peaks caused by motion artifacts, the IMU signal received from the third sensor 123 may be converted into the frequency domain by using FFT. For example, when receiving the PPG signal, the processor 110 may simultaneously receive the IMU signal and generate an IMU fragment by sampling the IMU signal based on a time window. In an embodiment, a timing and a period at which the IMU signal is sampled based on the time window may be the same as a timing and a period at which the PPG signal is sampled based on the time window.

The processor 110 may generate a power spectrum of the IMU signal in the frequency domain by converting the IMU fragment into the frequency domain by using FFT.

As shown, a power spectrum SP3 of the IMU signal may include the first peak P1 and the third peak P3. Accordingly, it may be seen that the first peak P1 and the third peak P3 in the first power spectrum SP1 are peaks caused by motion artifacts.

The processor 110 may cancel the third power spectrum SP3 from the first power spectrum SP1. In other words, the processor 110 may remove the first peak P1 and the third peak P3 in the third power spectrum SP3 from the first power spectrum SP1 to generate a second power spectrum SP2. Accordingly, the first peak P1 and the third peak P3 may be cancelled from among the first peak P1, the second peak P2, and the third peak P3, and the second power spectrum SP2 may include the second peak P2. A heart rate may be calculated based on a frequency of the second peak P2.

Figure 12:
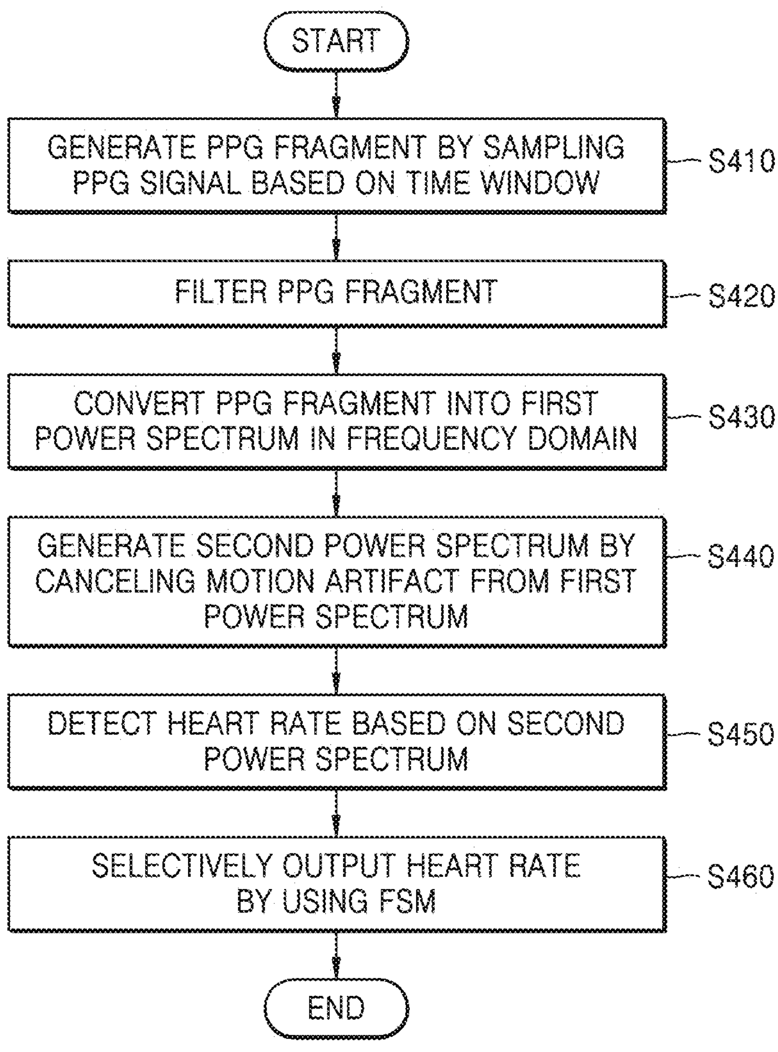
FIG. 12 is a flowchart showing window power spectrum analysis, according to an embodiment.

FIG. 12 is a flowchart showing window power spectrum analysis, according to an embodiment. The flowchart may include operations S410 to S460. The operations S410 to S460 of the embodiment of FIG. 12 may be performed by the electronic device 100 of FIGS. 1 and 3 and is described with reference to FIG. 1.

Referring to FIG. 12, the processor 110 may generate a PPG fragment by sampling a PPG signal based on a time window (S410). For example, the time window may be set to a certain time. The processor 110 may filter the PPG fragment (S420). The processor 110 may convert the PPG fragment into a first power spectrum in the frequency domain (S430) and cancel motion artifacts from the first power spectrum to generate a second power spectrum (S440). The processor 110 may detect a heart rate based on the second power spectrum (S450). Operations S410 to S450 are the same as operations S310 to S350 of FIG. 10, and repeated descriptions thereof are omitted for conciseness.

The processor 110 may selectively output a heart rate by using a finite state machine (FSM) (S460). For example, the processor 110 may determine whether the heart rate is stably detected using the FSM, and when determining that the heart rate is stably detected, the processor 110 may output the heart rate to detect atrial fibrillation. When determining that the heart rate is not stably detected, the processor 110 may discard the heart rate.

Figure 13:
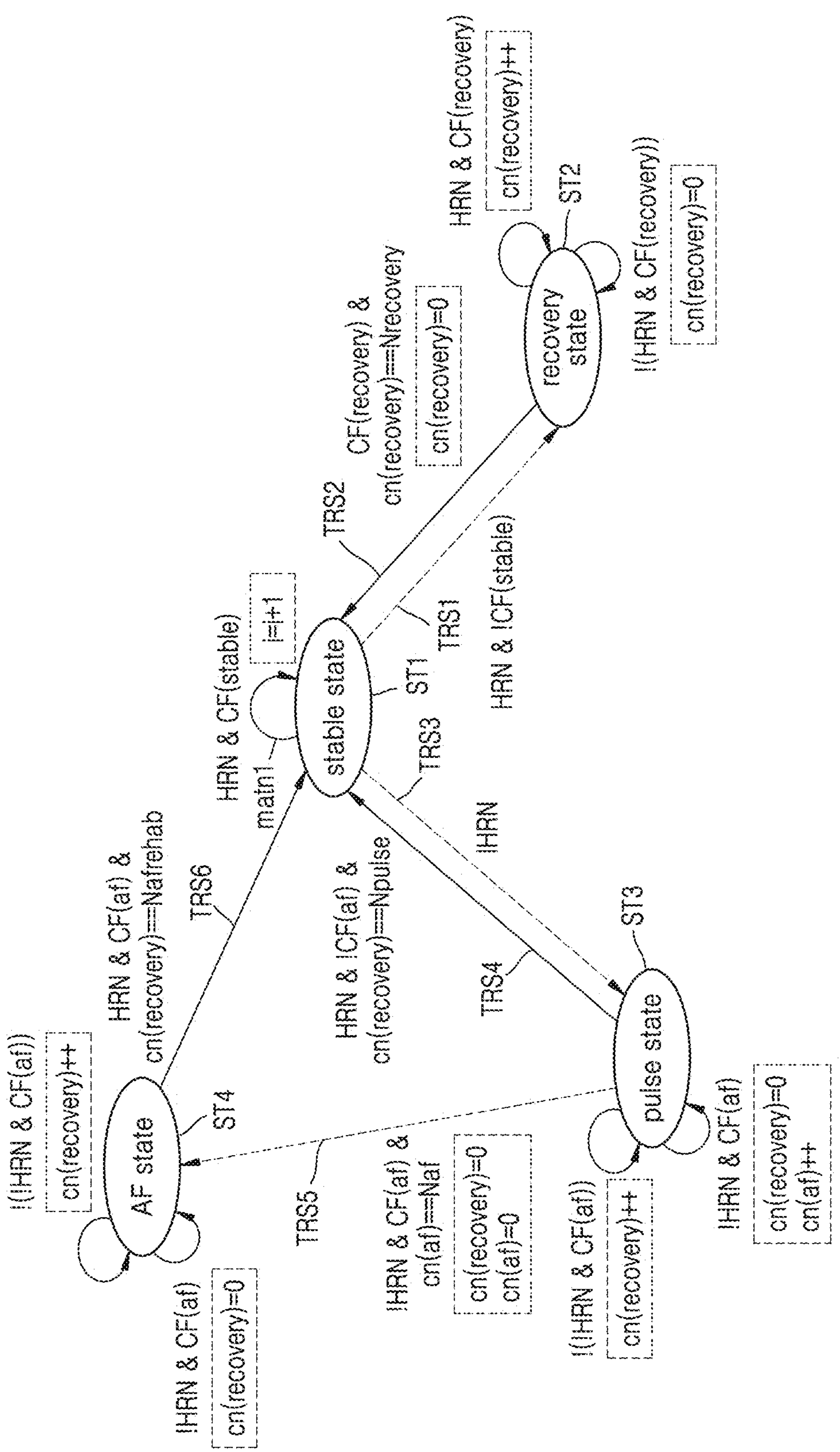
FIG. 13 shows a finite state machine (FSM), according to an embodiment.

FIG. 13 shows an FSM, according to an embodiment.

Referring to FIG. 13, the FSM is an algorithm for determining the reliability of a detected heart rate and may include a first state ST1, a second state ST2, a third state ST3, and a fourth state ST4. In an embodiment, the FSM may be executed by the processor 110 (in FIG. 1).

The first state ST1 may be a stable state, the second state ST2 may be a recovery state, the third state ST3 may be a pulse state, and the fourth state ST4 may be an atrial fibrillation (AF) state. The first state ST1 represents a state in which the heart rate is stably detected, that is, a state in which the PPG signal is stably measured. The second state ST2 represents a state in which the PPG signal is not stably measured and an incorrect heart rate is estimated to be detected. The third state ST3 represents a state in which there is a temporary abnormality in the heartbeat and it is necessary to check whether the PPG signal is measured from a user. The fourth state ST4 represents a state in which it is determined that although there is a temporary abnormality in the heartbeat, the PPG signal is measured from the user and the heart rate is stably detected.

Regardless of whether there is an abnormality in the heart rate, the first state ST1 and the fourth state ST4 represent a state in which the heart rate is stably detected and the second state ST2 and the third state ST3 represent a state in which the heart rate is not stably detected. Accordingly, the heart rates in the first state ST1 and the fourth state ST4 have high reliability and may thus be output to be used to detect atrial fibrillation. The heart rates in the second state ST2 and the third state ST3 have low reliability, and thus when the heart rates in the second state ST2 and the third state ST3 are used to detect atrial fibrillation, the accuracy of the atrial fibrillation detection result may be low. Accordingly, the heart rates of the second state ST2 and the third state ST3 may be not output and may be discarded.

When determining that the heart rate changes excessively in a short period of time, the processor 110 may determine that the PPG signal is not measured in a stable state and convert the current state in which the heart rate is detected into the second state ST2 or the third state ST3. The processor 110 may determine presence or absence of a dominant peak, which may be a signal due to the heartbeat, in the second power spectrum based on a crest factor that indicates how distinct the peak is, and when determining that there is no dominant peak, the processor 110 may perform conversion into a corresponding state depending on a previous state. Such state conversion may be performed by the FSM and is described in detail below with reference to FIG. 13.

In FIG. 13, HRN represents a normal heart rate variation, and CF (stable), CF (recovery), and CF (af) represent a crest factor of the first state ST1, the second state ST2, and the fourth state ST4, respectively. An exclamation (!) before a term indicates that a condition is not satisfied, and for example, "!HRN" means not a normal heart rate variation, that is, an abnormal heart rate variation. cn (recovery) represents the number of times a recovery condition, such as a condition for the second state ST2, the third state ST3, and the fourth state ST4 to be converted into the first state ST1, is satisfied, and Nrecovery, Npulse, and Nafrehab represent the number of times cn (recovery) needs to be reached for the second state ST2, the third state ST3, and the fourth state ST4 to be converted into the first state ST1. cn(af) represents the number of times the third state ST3 satisfies a condition for conversion to the fourth state ST4, and Naf represents the number of times that cn(af) needs to be reached for the third state ST3 to be converted into the fourth state ST4.

Based on the heart rate variation ΔHR, normal heart rate variation HRN may be determined. According to Equation 1, the absolute value of the difference between the current (i-th) heart rate HR(i) and a previous (i−1th) heart rate HR(i−1) may be calculated as the heart rate variation ΔHR. Here, the previous heart rate HR(i−1) is a heart rate output to detect atrial fibrillation.

$$\Delta HR = |HR(i) - HR(i-1)| \quad \text{Equation 1}$$

When the heart rate variation ΔHR is less than a threshold set for a heart rate variation, it may be determined that the heart rate variation is not large (normal heart rate variation HRN), and when the heart rate variation ΔHR is equal to or greater than the threshold, it may be determined that the heart rate variation is large (abnormal heart rate variation-!HRN).

For example, when the threshold is set to 5, the current heart rate HR(i) is 75 BPM, and when a previous heart rate HR(i−1) is 78 BPM, the heart rate variation (ΔHR) is 3, and thus it may be determined that the heart rate variation is not large (normal heart rate variation HRN).

A crest factor CF may be calculated according to Equation 2.

$$CF(i) = Xpeak(i)/Xrms(i) \quad \text{Equation 2}$$

Here, CF(i) represents a crest factor in a second frequency spectrum of the PPG fragment in which the current heart rate HR(i) is detected, Xpeak(i) represents a power value of the frequency with the highest power in the second frequency spectrum, and Xrms(i) represents an average power of all frequencies of the second frequency spectrum. In other words, the crest factor indicates how much greater power at a specific frequency than the average power in all frequency sections of a frequency range.

A first threshold THstable, a second threshold THrecovery, and a third threshold THaf for determining crest factors in the first state, the second state, and the fourth state may be set. When CF(i) is greater than the first threshold THstable, CF(i) may be estimated to be a crest factor CF(stable) in the first state, when CF(i) is less than or equal to the first threshold THstable and greater than the second threshold THrecovery, CF(i) may be estimated to be a crest factor CF(recovery) in the second state, and when CF(i) is less than or equal to the second threshold THrecovery and greater than the third threshold THaf, CF(i) may be estimated to be a crest factor CF(af) in the fourth state.

In the first state ST1, a dominant peak to be a heart rate signal exists in the second power spectrum, and the heart rate variation is normal. For example, when a previous state (a state in which the previous heart rate (HR(i−1)) is detected) is the first state ST1 and the current heart rate HR(i) is detected, the heart rate variation is normal (HRN), and when CF(i) is the crest factor CF(stable) in the first state, the current state may be maintained in the first state ST1 (matn1).

In the second state ST2, there is no dominant peak in the second power spectrum, and the heart rate variation may be normal. At this time, the detected heart rate may be noise resulting from motion artifacts rather than a heart rate signal.

When a previous state is the first state ST1, CF(i) is not the crest factor CF(stable) in the first state (!CF(stable)), and when the heart rate variation is normal (HRN), the first state ST1 may be converted into the second state ST2 (TRS1). The current heart rate HR(i) may not be output and may be discarded.

The current heart rate HR(i) may be recalculated based on a PPG fragment generated after the PPG fragment in which the current heart rate HR(i) is detected, and based on the recalculated current heart rate HR(i), the heart rate variation and the current crest factor CF(i) may be calculated. When the heart rate variation is normal (HRN) and the current crest factor CF(i) is a crest factor CF(recovery) in the second state, a first recovery condition CF(recovery)&HRN in which the second state ST2 is converted into the first state ST1 is satisfied. Cn (recovery) may increase (cn(recovery)++). When the first recovery condition CF(recovery) &HRN is continuously satisfied several times and cn(recovery) reaches Nrecovery, the second state ST2 may be converted into the first state ST1 (TRS2). When the current state is converted into the first state ST1 or the first recovery condition CF(recovery)&HRN is not satisfied (!(CF(recovery)& HRN)), cn(recovery) may be initialized to 0 (cn (recovery)=0).

When a previous state is the first state ST1, if the heart rate variation is not normal (!HRN), the first state ST1 may be converted into the third state ST3 (TRS3). The current heart rate HR(i) may not be output and may be discarded.

Then, when the heart rate variation is normal (HRN) and the current crest factor CF(i) is not the crest factor CF(af) in the fourth state (!CF(af)), a second recovery condition HRN & !CF(af) in which the third state ST3 is converted into the first state ST1 is satisfied. When the second recovery condition HRN & !CF(af) is continuously satisfied several times and cn(recovery) reaches Npulse, the third state ST3 may be converted into the first state ST1 (TRS4).

When the heart rate variation is abnormal (!HRN) and the current crest factor CF(i) is the crest factor CF(af) in the fourth state, a first determination condition!HRN & CF(af) in which the third state ST3 is converted into the fourth state ST4 is satisfied. When the first determination condition-!HRN & CF(af) is continuously satisfied several times and cn(af) reaches Naf, the third state ST3 may be converted into the fourth state ST4 (TRS5).

The fourth state ST4 is a state in which the heart rate variation is large and CF(af) is continuously satisfied and is determined to be a state in which there is cardiac physiological abnormality but the heart rate is stably detected. Then, when the heart rate variation is normal (HRN) and the current crest factor CF(i) is the crest factor CF(af) in the fourth state, a third recovery condition HRN & CF(af) in which the fourth state ST4 is converted into the first state ST1 is satisfied. When the third recovery condition HRN & CF(af) is continuously satisfied several times and cn(recovery) reaches Nafrehab, the fourth state ST4 may be converted into the first state ST1 (TRS6). In other words, when the current crest factor CF(i) is maintained in the crest factor CF(af) in the fourth state and the heart rate variation is stable, the fourth state ST4 may be converted into the first state ST1 (TRS6).

In the first state ST1 and fourth state ST4, the current heart rate HR(i) is output, and in the second state ST2 and the third state ST3, it may be determined that the heart rate is not stably detected, the detected current heart rate HR(i) may be discarded, and the current heart rate HR(i) may be re-detected (recalculated). Accordingly, when determining that heart rates with high reliability, in other words, the PPG signal in a stable state is measured, the processor 110 may detect atrial fibrillation based on detected heart rates, thereby improving the accuracy of atrial fibrillation detection.

Figure 14:
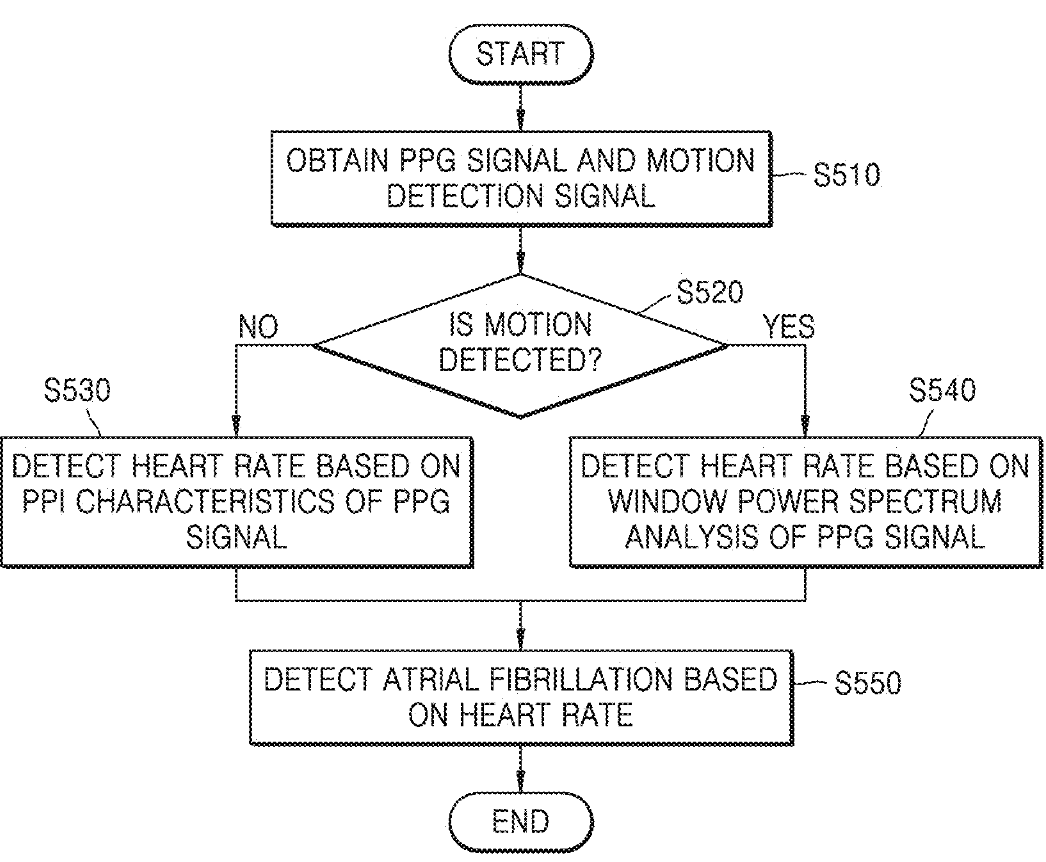
FIG. 14 is a flowchart showing a method of detecting atrial fibrillation, according to an embodiment.
Figure 15:
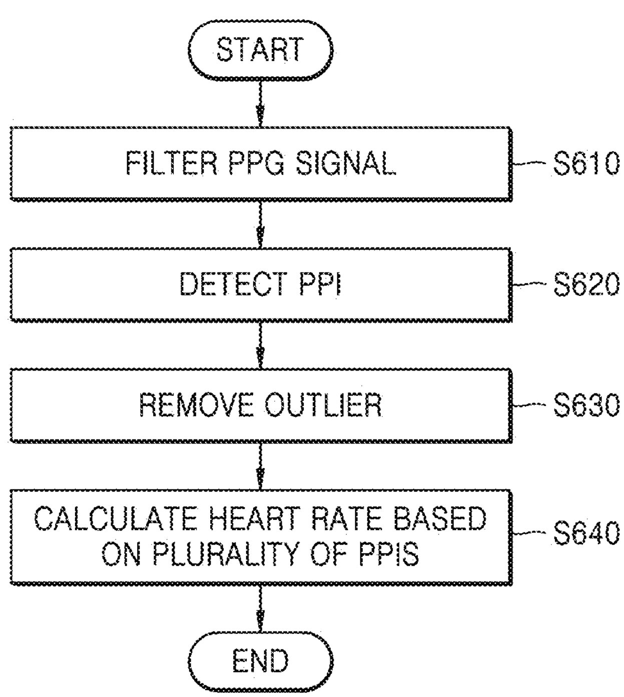
FIG. 15 is a flowchart showing a method for detecting a heart rate based on the peak-peak interval (PPI) characteristics of a PPG signal, according to an embodiment.

FIG. 14 is a flowchart showing a method of detecting atrial fibrillation, according to an embodiment. FIG. 15 is a flowchart showing a method for detecting a heart rate based on the PPI characteristics of a PPG signal. The flowchart of FIG. 14 may include operations S510 to S550, and the flowchart of FIG. 15 may include operations S610 to S640. The operations S510 to S550 and operations S610 to S640 of the embodiment of FIGS. 14 and 15 may be performed by the electronic device 100 of FIGS. 1 and 3 and is described with reference to FIG. 1.

Referring to FIG. 14, the electronic device 100 may obtain a PPG signal and a motion detection signal (S510). For example, the processor 110 may receive a PPG signal from the first sensor 121 and an IMU signal from the third sensor 123.

The electronic device 100 may check whether motion is detected (S520). For example, the processor 110 may determine whether there is user motion based on an IMU signal from the third sensor 123. For example, the processor 110 may calculate motion artifacts of the IMU signal, and when the motion artifact exceeds a reference value, it may be determined that there is motion, and when the motion artifact is less than or equal to the reference value, it may be determined that there is no motion. The reference value may be preset.

When no motion is detected (i.e., when the motion artifact is less than or equal to the reference value) (operation S520, NO), the electronic device 100 may detect a heart rate based on the PPI characteristics of the PPG signal (S530). Referring to FIG. 15, the processor 110 (or the sensing circuit 25 of FIG. 2) may perform filtering on the PPG signal to remove noise (S610). For example, as a noise removal filter, an infinite impulse response (IIR) filter, a moving average filter, and a heart rate (HR) range filter may be used.

The processor 110 may detect the PPI of the filtered PPG signal (S620). As shown in FIG. 4A, a duration between peaks P of two adjacent pulses among a plurality of pulses of the filtered PPG signal may be detected as a PPI.

The processor 110 may remove outliers from among the plurality of detected PPIs (S630). It is highly likely that the outliers are caused by noise. Therefore, outliers may be removed to improve the accuracy of the heart rate. For example, when a difference with other adjacent PPIs is equal to or greater than a set removal threshold, the corresponding PPI may be determined to be an outlier and removed.

The processor 110 may calculate a heart rate based on the plurality of detected PPIs (S640).

Continuing to refer to FIG. 14, when motion is detected (i.e., when the motion artifact is greater than to the reference value) (operation S520, YES), the electronic device 100 may detect a heart rate based on window power spectrum analysis of the PPG signal (S540). As described with reference to FIGS. 6 to 13, the electronic device 100 may detect a heart rate based on window power spectrum analysis of the PPG signal. The PPG signal may be sampled based on a time window, generated as a PPG fragment, and the PPG fragment may be converted into a power spectrum in the frequency domain. Motion artifacts may be cancelled from the power spectrum, and highly reliable heart rates may be output based on an FSM.

The electronic device 100 may detect atrial fibrillation based on the detected heart rate (S550). For example, the processor 110 may check whether atrial fibrillation occurs based on the detected heart rate.

Figure 16:
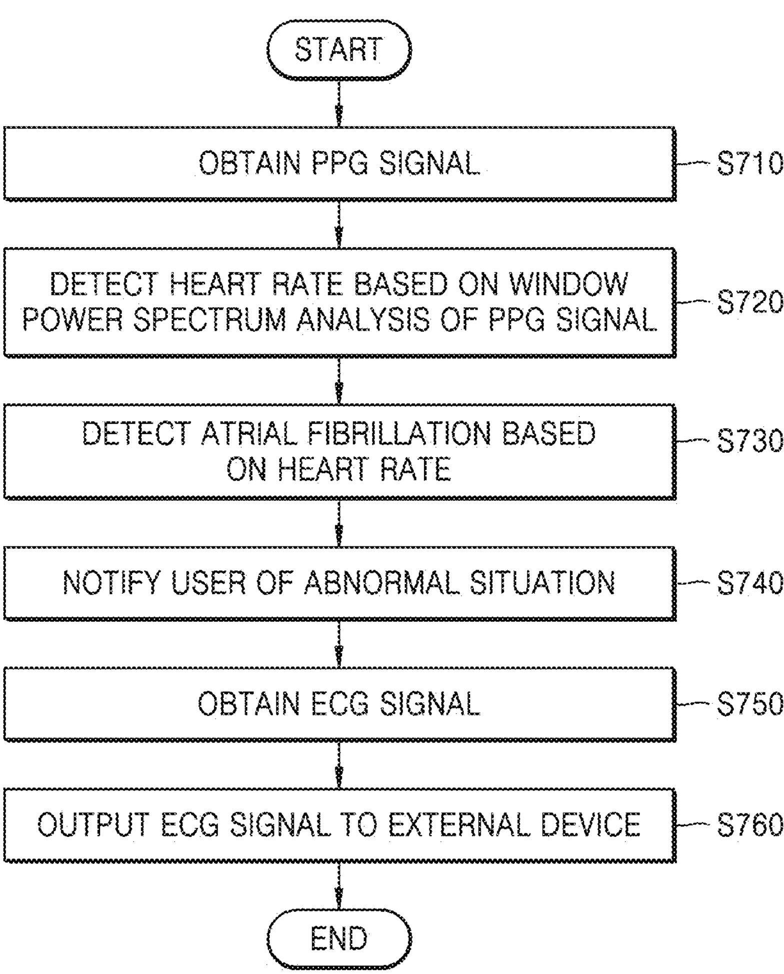
FIG. 16 is a flowchart showing an operating method of an electronic device, according to an embodiment.

FIG. 16 is a flowchart showing an operating method of an electronic device, according to an embodiment. The method may include operations S710 to S760. The operations S710 to S760 of the method shown in FIG. 16 may be performed by the electronic device of FIG. 1.

Referring to FIG. 16, the electronic device 100 may obtain a PPG signal (S710) and detect a heart rate based on window power spectrum analysis of the PPG signal (S720). The electronic device 100 may detect atrial fibrillation based on the detected heart rates (S730). Operations S710, S720, and S730 are the same as operations S110, S130, and S150 of FIG. 5. Therefore, repeated descriptions thereof are omitted for conciseness.

When atrial fibrillation is detected, the electronic device 100 may notify a user of an abnormal situation (S740). For example, the electronic device 100 may output event information notifying occurrence of an abnormal situation, that is, detection of atrial fibrillation, to the user through the display 131.

The electronic device 100 may obtain an ECG signal (S750). The user may check abnormal situation notifications and touch an electrode of the second sensor 122 with a part of the body (e.g., a finger) to measure ECG. The electronic device 100 may measure ECG and generate an ECG signal. As such, the electronic device 100 may obtain the ECG signal in response to detection of atrial fibrillation.

The electronic device 100 may output the ECG signal to an external device (S760). As described above, whether atrial fibrillation occurs may be monitored at all times based on PPG. However, more accurate diagnosis of atrial fibrillation may be performed when medical staff analyzes the ECG signal. Accordingly, the electronic device 100 may output the ECG signal to an external device to allow medical staff to diagnose atrial fibrillation based on the ECG signal. In some embodiments, the external device may be, for example, a medical staff server. In some embodiments, the external device may be a mobile device such as a smartphone, and the ECG signal may be transmitted to the medical staff server through the mobile device.

Figure 17A:
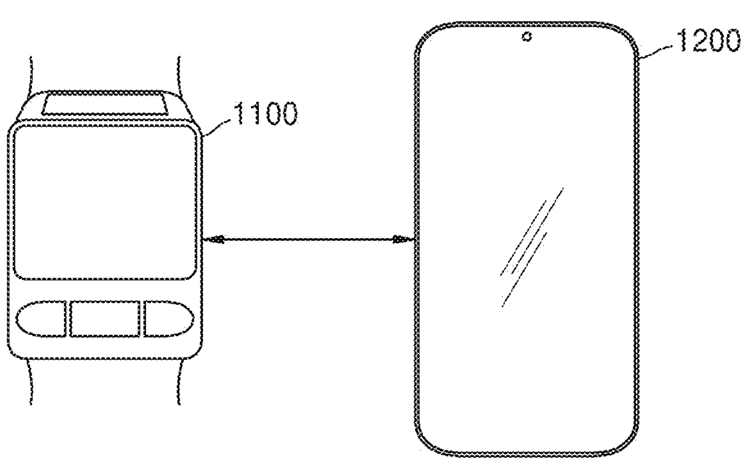
FIGS. 17A and 17B illustrate a biological signal monitoring system, according to some embodiments.
Figure 17B:
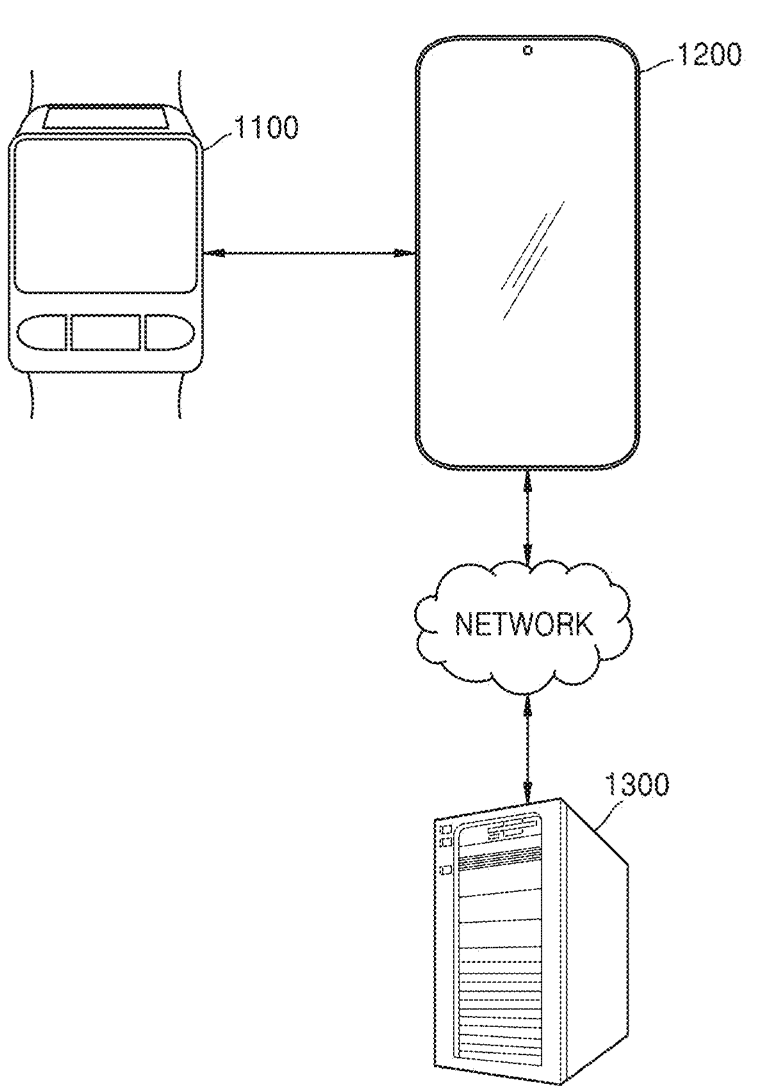

FIGS. 17A and 17B illustrate biological signal monitoring systems, according to some embodiments.

Referring to FIGS. 17A and 17B, biological signal monitoring systems 1000*a* and 1000*b* may include a biological signal monitoring device 1100 and a data receiving device 1200. The biological signal monitoring system 1000*b* may further include a server 1300.

The electronic device 100 described with reference to FIG. 1, for example, a wearable device, may be applied to the biological signal monitoring device 1100. Accordingly, the above description of the electronic device 100 and an operation thereof may be applied to the biological signal monitoring device 1100 and repeated description thereof is omitted for conciseness. The data receiving device 1200 may be an electronic device including a mobile communication interface, such as a smartphone, a tablet PC, or a mobile communication device. The server 1300 may be, for example, a medical staff server or a cloud server.

The biological signal monitoring device 1100 may measure a PPG signal, an ECG signal, and a motion detection signal (e.g., an IMU signal). The biological signal monitoring device 1100 may detect a heart rate through window power spectrum analysis of the PPG signal and detect atrial fibrillation based on the heart rate. The biological signal monitoring device 1100 may continuously monitor whether atrial fibrillation occurs based on the PPG signal. In an embodiment, the biological signal monitoring device 1100 may cancel motion artifacts from the PPG signal based on the motion detection signal. In an embodiment, when determining that atrial fibrillation occurs, the biological signal monitoring device 1100 may output event information notifying occurrence of an abnormal situation, that is, detection of atrial fibrillation, to the user through a display and/or a speaker. When the user touches an electrode to measure the ECG with a part of the body, the biological signal monitoring device 1100 may measure ECG and transmit the ECG signal to the data receiving device 1200 through a wired or wireless short-range communication interface.

The data receiving device 1200 may transmit an ECG signal (or signal-processed ECG data) to the server 1300. In an embodiment, the biological signal monitoring device 1100 may include a mobile communication interface and may transmit an ECG signal directly to the server 1300. Medical staff may detect (diagnose) atrial fibrillation based on the ECG signal transmitted to the server 1300.

As described above, the electronic device 100 (in FIG. 1) and the biological signal monitoring device 1100 (in FIGS. 17A and 17B) may detect atrial fibrillation based on the PPG signal, and when there is motion, the electronic device 100 and the biological signal monitoring device 1100 may cancel motion artifacts from the PPG signal by using a window power spectrum method in the frequency domain, and may detect a heart rate through window power spectrum analysis and detect atrial fibrillation based on highly reliable heart rates by using an FSM. Accordingly, the electronic device 100 and the biological signal monitoring device 1100 may continuously monitor whether atrial fibrillation occurs, and the accuracy of atrial fibrillation detection based on the PPG signal may be improved. The electronic device 100 and the biological signal monitoring device 1100 may measure an ECG when detecting atrial fibrillation based on the PPG signal and transmit the ECG signal to an external electronic device or a medical staff server for diagnosing atrial fibrillation. Accordingly, the continuity and accuracy of atrial fibrillation detection may be improved.

Various embodiments have been described in the drawings and specification. Although various embodiments have been described in this specification using specific terms, these terms are only used for the purpose of explaining the technical ideas of the present disclosure and is not used to limit the meaning or scope as set forth in the appended claims. Therefore, those skilled in the art will understand that various modifications and other equivalent embodiments are possible therefrom. Therefore, the true technical protection scope should be determined by the technical spirit of the attached claims.

While various embodiments have been particularly shown and described with reference to the drawings, it will be understood that various changes in form and details may be made therein without departing from the spirit and scope of the following claims.

What is claimed is:

1. A method of detecting atrial fibrillation, the method comprising:

receiving a photoplethysmogram (PPG) signal from a first sensor of a wearable device;

detecting a heart rate from the PPG signal based on a window power spectrum analysis of the PPG signal;

determining, based on a finite state machine, a state in which the heart rate is detected;

outputting the heart rate to be used to detect the atrial fibrillation based on the state indicating that the heart rate is stably calculated; and detecting atrial fibrillation based on the heart rate that is output, wherein the finite state machine includes a stable state, a recovery state, a pulse state, and an atrial fibrillation state, and the heart rate is output in the stable state or the atrial fibrillation state, and the heart rate is discarded in the recovery state or the pulse state.

2. The method of claim 1, wherein detecting the heart rate includes:

generating a PPG fragment by sampling the PPG signal based on a time window;

converting the PPG fragment into a first power spectrum of a frequency domain;

canceling a motion artifact from the first power spectrum to generate a second power spectrum; and estimating the heart rate based on the second power spectrum.

3. The method of claim 2, wherein estimating the heart rate includes converting a frequency having a peak value in the second power spectrum into the heart rate.

4. The method of claim 2, wherein cancelling the motion artifact includes:

converting a motion detection signal received from a second sensor of the wearable device into a third power spectrum in the frequency domain; and cancelling the third power spectrum from the first power spectrum to generate the second power spectrum.

5. The method of claim 1, wherein the state in which the heart rate is detected is transitioned between the stable state, the recovery state, the pulse state, and the atrial fibrillation state based on presence or absence of a dominant peak in a second power spectrum, a crest factor of the dominant peak, and a heart rate variation.

6. The method of claim 2, wherein generating the PPG fragment includes generating a plurality of PPG fragments via sliding of the PPG signal at certain time intervals in the time window, wherein the plurality of PPG fragments include a first PPG fragment and a second PPG fragment, and wherein the first PPG fragment and the second PPG fragment partially overlap in time.

7. The method of claim 6, wherein a plurality of heart rates are detected from the plurality of PPG fragments, and wherein detecting the atrial fibrillation includes performing stochastic analysis on the plurality of heart rates.

8. The method of claim 1, further comprising detecting presence or absence of motion based on a motion detection signal received from a second sensor of the wearable device, wherein detecting the heart rate includes detecting the heart rate from the PPG signal based on peak-peak interval (PPI) characteristics of the PPG signal when there is no motion.

9. The method of claim 1, further comprising:

obtaining an electrocardiogram (ECG) signal through a third sensor of the wearable device, in response to detecting the atrial fibrillation; and transmitting the ECG signal to an external device for performing an atrial fibrillation diagnosis based on the ECG signal.

10. A method of detecting atrial fibrillation, the method comprising:

obtaining a photoplethysmogram (PPG) signal from a first sensor of a wearable device;

obtaining a motion detection signal from a second sensor of the wearable device;

determining whether there is motion exceeding a reference value, based on the motion detection signal;

detecting a heart rate from the PPG signal based on a peak-peak interval (PPI) of the PPG signal when the motion does not exceed the reference value and based on power spectrum analysis in a frequency domain of the PPG signal when the motion exceeds the reference value;

detecting atrial fibrillation based on the heart rate;

identifying, using a finite state machine including a stable state, a recovery state, a pulse state, and an atrial fibrillation state, a state in which the heart rate is calculated;

when the state is the stable state or the atrial fibrillation state, outputting the heart rate to be used in detecting the atrial fibrillation; and when the state is the recovery state or the pulse state, not outputting the heart rate and discarding the heart rate.

11. The method of claim 10, further comprising obtaining an electrocardiogram (ECG) signal through a third sensor of the wearable device based on detecting the atrial fibrillation; and transmitting the ECG signal to an external device for performing an atrial fibrillation diagnosis based on the ECG signal.

12. The method of claim 10, wherein the motion exceeds the reference value and detecting the heart rate from the PPG signal based on the power spectrum analysis includes:

generating a PPG fragment and a motion fragment by sampling the PPG signal and the motion detection signal based on a time window;

converting the PPG fragment and the motion fragment into a first power spectrum and a second power spectrum in the frequency domain, respectively;

canceling the second power spectrum from the first power spectrum to generate a third power spectrum; and estimating the heart rate based on the third power spectrum.

13. The method of claim 10, wherein a current state is transitioned between the stable state, the recovery state, the pulse state, and the atrial fibrillation state based on presence or absence of a dominant peak in a second power spectrum, a crest factor of the dominant peak, and a heart rate variation.

14. The method of claim 10, wherein detecting the heart rate includes:

performing stochastic analysis on a plurality of heart rates detected from a plurality of PPG fragments that overlap each other in time.

15. A wearable device comprising:

a first sensor configured to sense a pulse wave of a user and generate a photoplethysmogram (PPG) signal based on the pulse wave;

a second sensor configured to sense motion of the user and generate a motion detection signal;

a memory storing program code; and at least one processor configured to access the memory to execute the program code, wherein the program code causes at least one of the at least one processor to detect a heart rate based on a peak-peak interval (PPI) of the PPG signal when the second sensor senses no motion and based on power spectrum analysis of the PPG signal in a frequency domain when the second sensor senses the motion, and wherein the program code causes at least one of the at least one processor to detect atrial fibrillation based on the heart rate, and wherein:

the program code causes at least one of the at least one processor to identify, using a finite state machine including a stable state, a recovery state, a pulse state, and an atrial fibrillation state, a state in which the heart rate is calculated, when the state is the stable state or the atrial fibrillation state, the program code causes at least one of the at least one processor to output the heart rate to be used in detecting the atrial fibrillation; and when the state is the recovery state or the pulse state, the program code causes at least one of the at least one processor to not output the heart rate and discard the heart rate.

16. The wearable device of claim 15, further comprising:

a third sensor configured to sense an ECG of the user and generate an electrocardiogram (ECG) signal based on the ECG;

a display; and a communication interface, wherein, based on detecting the atrial fibrillation, the program code causes at least one of the at least one processor to control the third sensor to sense the ECG and generate the ECG signal and control the communication interface to transmit the ECG signal to an external device for atrial fibrillation diagnosis.

17. The wearable device of claim 15, wherein:

the program code causes at least one of the at least one processor to generate a PPG fragment and a motion fragment by sampling the PPG signal and the motion detection signal based on a time window when the second sensor senses the motion, the program code causes at least one of the at least one processor to convert the PPG fragment and the motion fragment into a first power spectrum and a second power spectrum in the frequency domain, respectively and to generate a third power spectrum by canceling the second power spectrum from the first power spectrum, and the program code causes at least one of the at least one processor to estimate the heart rate based on the third power spectrum.

* * * * *